(12) United States Patent
Pegg et al.

(10) Patent No.: US 10,428,065 B2
(45) Date of Patent: Oct. 1, 2019

(54) ISOXAZOLYL SUBSTITUTED IMIDAZOPYRIDINES

(71) Applicant: CELLCENTRIC LTD, Cambridge, Cambridgeshire (GB)

(72) Inventors: Neil Anthony Pegg, Cambridge (GB); David Michel Adrien Taddei, Nottingham (GB); Richard Brown, Nottingham (GB)

(73) Assignee: CELLCENTRIC LTD, Cambridge, Cambridgeshire (GB)

(*) Notice: Subject to any disclaimer, the term of this patent is extended or adjusted under 35 U.S.C. 154(b) by 0 days.

(21) Appl. No.: 15/567,750

(22) PCT Filed: Apr. 20, 2016

(86) PCT No.: PCT/GB2016/051087
§ 371 (c)(1),
(2) Date: Oct. 19, 2017

(87) PCT Pub. No.: WO2016/170323
PCT Pub. Date: Oct. 27, 2016

(65) Prior Publication Data
US 2018/0105519 A1    Apr. 19, 2018

(30) Foreign Application Priority Data
Apr. 20, 2015  (GB) .................................. 1506660.8

(51) Int. Cl.
*C07D 471/04*     (2006.01)
*A61P 35/00*      (2006.01)

(52) U.S. Cl.
CPC ............ *C07D 471/04* (2013.01); *A61P 35/00* (2018.01)

(58) Field of Classification Search
CPC .................................................. C07D 471/04
See application file for complete search history.

(56) References Cited

U.S. PATENT DOCUMENTS

| | | |
|---|---|---|
| 3,538,097 A | 11/1970 | Loewe et al. |
| 5,667,975 A | 9/1997 | Dykstra et al. |
| 5,770,617 A | 6/1998 | LaVoie et al. |
| 6,313,312 B1 | 11/2001 | Banks et al. |
| 6,548,505 B1 | 4/2003 | Martin et al. |
| 2003/0010971 A1 | 1/2003 | Zhang et al. |
| 2005/0101647 A1 | 5/2005 | Oda et al. |
| 2005/0256157 A1 | 11/2005 | Gesner et al. |
| 2005/0261307 A1 | 11/2005 | Cai et al. |
| 2007/0112048 A1 | 5/2007 | Bavari et al. |
| 2008/0274418 A1 | 11/2008 | Lin et al. |
| 2010/0316607 A1 | 12/2010 | Or et al. |
| 2011/0046982 A1 | 2/2011 | Arya et al. |

(Continued)

FOREIGN PATENT DOCUMENTS

| | | |
|---|---|---|
| CN | 103728294 A | 4/2014 |
| CN | 103880823 A | 6/2014 |

(Continued)

OTHER PUBLICATIONS

Hay "Discovery and Optimization of Small-Molecule Ligands for the CBP/p300 Bromodomains." Journal of the American Chemical Society, 2014, 136(26), 9308-9319.*
Wermuth, Camille G. "Molecular Variation Based on Isosteric Replacements" in Chapter 13, The Practice of Medicinal Chemistry, Academic: 1996, pp. 203-237.*
Fedorov, "[1,2,4]Triazolo[4,3-a]phthalazines: Inhibitors of diverse bromodomains." J. Med. Chem. 57, 462-476 (2014).*
International Search Report and Written Opinion dated Jun. 7, 2016 from International Application No. PCT/GB2016/051087, 10 pages.
UK Intellectual Property Office Search Report dated Jan. 15, 2016 for GB1506660.8, 5 pages.
Bedford et al., "Ubiquitin-like protein conjugation and the ubiquitin-proteasome system as drug targets", Nature Reviews Drug Discovery, Jan. 2011, vol. 10, No. 1, pp. 29-46.
Paul Brennan, "Isoxazole Inhibitors of Bromodomains", SGC Oxford, Nuffield Dept. of Clinical Medicine, University of Oxford, presented at RSC Advances in Synthesis and Medicinal Chemistry, May 1, 2012, 46 pages.
Cai et al., "Intratumoral De Novo Steroid Synthesis Activates Androgen Receptor in Castration-Resistant Prostate Cancer and Is Upregulated by Treatment with CYP17A1 Inhibitors", Cancer Research, Oct. 15, 2011, vol. 71, No. 20, pp. 6503-6513.

(Continued)

*Primary Examiner* — David K O'Dell
(74) *Attorney, Agent, or Firm* — MH2 Technology Law Group, LLP

(57) ABSTRACT

A compound which is an isoxazolyl imidazopyridine of formula (I): wherein: $R^0$ and R, which are the same or different, are each H or C alkyl; $R^{9'}$ and $R^{9''}$, which are the same or different, are each H or F; X is -(alk)$_n$-, -alk-C(=O)—NR—, -alk-NR—C(=O)— or -alk-C(=O)—; $R^1$ is selected from —S(=O)$_2$R' and a 4- to 7-membered heterocyclic group which is unsubstituted or substituted; $R^2$ and $R^{2'}$, which are the same or different, are each H or $C_{1-6}$ alkyl; or $R^2$ and $R^{2'}$ form, together with the C atom to which they are attached, a $C_{3-6}$ cycloalkyl group; $R^3$ and $R^{3'}$, which are the same or different, are each H, $C_{1-6}$ alkyl, OH or F; $R^4$ is phenyl or a 5- to 12-membered N-containing heteroaryl group and is unsubstituted or substituted; alk is $C_{1-6}$ alkylene; R' is $C_{1-6}$ alkyl; and n is 0 or 1; or a pharmaceutically acceptable salt thereof. The compound has activity in modulating the activity of p300 and/or CBP and is used to treat cancer.

(I)

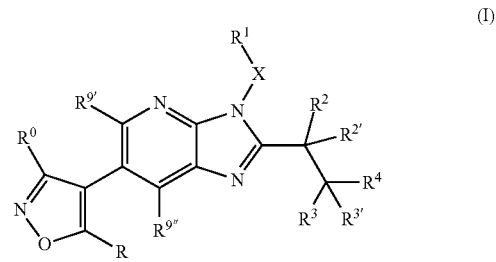

5 Claims, No Drawings

(56) References Cited

U.S. PATENT DOCUMENTS

| | | |
|---|---|---|
| 2011/0092415 A1 | 4/2011 | DeGoey et al. |
| 2012/0230951 A1 | 9/2012 | Alam et al. |
| 2014/0142798 A1 | 5/2014 | Guamizo Martinez et al. |
| 2014/0364429 A1 | 12/2014 | Zhan |

FOREIGN PATENT DOCUMENTS

| | | |
|---|---|---|
| CN | 103952009 A | 7/2014 |
| CN | 104030988 A | 9/2014 |
| CN | 104193738 A | 12/2014 |
| CN | 104710410 A | 6/2015 |
| CN | 104803989 A | 7/2015 |
| EP | 1460067 A1 | 9/2004 |
| FR | 1519964 A | 4/1968 |
| JP | 2000292930 A | 10/2000 |
| JP | 2004024114 A | 1/2004 |
| JP | 2009005594 A | 1/2009 |
| JP | 2015088313 A | 5/2015 |
| KR | 10-2010-0099459 | 9/2010 |
| WO | 90/12321 | 10/1990 |
| WO | 96/06831 | 3/1996 |
| WO | 96/40114 | 12/1996 |
| WO | 96/40145 | 12/1996 |
| WO | 97/04776 | 2/1997 |
| WO | 98/33503 | 8/1998 |
| WO | 98/38170 | 9/1998 |
| WO | 99/41241 | 8/1999 |
| WO | 00/66528 | 11/2000 |
| WO | 01/32630 A1 | 5/2001 |
| WO | 01/46175 A1 | 6/2001 |
| WO | 01/53268 A2 | 7/2001 |
| WO | 01/85724 A1 | 11/2001 |
| WO | 02/055025 A2 | 7/2002 |
| WO | 03/017994 A1 | 3/2003 |
| WO | 03/048140 A1 | 6/2003 |
| WO | 2004/014881 A2 | 2/2004 |
| WO | 2004/018419 A2 | 3/2004 |
| WO | 2005/012288 A1 | 2/2005 |
| WO | 2005/033065 A1 | 4/2005 |
| WO | 2005/047244 A2 | 5/2005 |
| WO | 2005/080348 A1 | 9/2005 |
| WO | 2005/082894 A1 | 9/2005 |
| WO | 2005/086754 A2 | 9/2005 |
| WO | 2006/028269 A2 | 3/2006 |
| WO | 2006/033943 A2 | 3/2006 |
| WO | 2006/130673 A1 | 12/2006 |
| WO | 2007/027594 A1 | 3/2007 |
| WO | 2007/070173 A2 | 6/2007 |
| WO | 2008/074091 A1 | 6/2008 |
| WO | 2008/129007 A1 | 10/2008 |
| WO | 2008/140239 A1 | 11/2008 |
| WO | 2009/005551 A2 | 1/2009 |
| WO | 2009/087379 A2 | 7/2009 |
| WO | 2009/105140 A2 | 8/2009 |
| WO | 2009/152072 A1 | 12/2009 |
| WO | 2010/065674 A9 | 6/2010 |
| WO | 2010/065681 A1 | 6/2010 |
| WO | 2010/075376 A2 | 7/2010 |
| WO | 2010/096777 A1 | 8/2010 |
| WO | 2010/132684 A9 | 11/2010 |
| WO | 2010/148006 A1 | 12/2010 |
| WO | 2011/007756 A1 | 1/2011 |
| WO | 2011/031904 A1 | 3/2011 |
| WO | 2011/075607 A1 | 6/2011 |
| WO | 2011/099832 A2 | 8/2011 |
| WO | 2011/119853 A1 | 9/2011 |
| WO | 2011/119858 A1 | 9/2011 |
| WO | 2011/119870 A1 | 9/2011 |
| WO | 2011/151618 A2 | 12/2011 |
| WO | 2012/044043 A2 | 4/2012 |
| WO | 2012/044567 A2 | 4/2012 |
| WO | 2012/051361 A1 | 4/2012 |
| WO | 2012/083170 A1 | 6/2012 |
| WO | 2012/135799 A1 | 10/2012 |
| WO | 2012/156284 A1 | 11/2012 |
| WO | 2012/167053 A1 | 12/2012 |
| WO | 2013/010904 A1 | 1/2013 |
| WO | 2013/036749 A1 | 3/2013 |
| WO | 2013/049567 A1 | 4/2013 |
| WO | 2013/052362 A1 | 4/2013 |
| WO | 2013/055607 A1 | 4/2013 |
| WO | 2013/059278 A2 | 4/2013 |
| WO | 2013/074387 A1 | 5/2013 |
| WO | 2013/093484 A1 | 6/2013 |
| WO | 2013/0114332 A1 | 8/2013 |
| WO | 2013/149997 A1 | 10/2013 |
| WO | 2014/019344 A1 | 2/2014 |
| WO | 2014/048072 A1 | 4/2014 |
| WO | 2014/081280 A2 | 5/2014 |
| WO | 2014/082381 A1 | 6/2014 |
| WO | 2014/125651 A1 | 8/2014 |
| WO | 2014/134240 A1 | 9/2014 |
| WO | 2014/151936 A1 | 9/2014 |
| WO | 2015/002754 A2 | 1/2015 |
| WO | 2015/009678 A2 | 1/2015 |
| WO | WO-2015002754 A2 * | 1/2015 ............ A61K 31/52 |
| WO | 2015/022332 A1 | 2/2015 |
| WO | 2015/031819 A1 | 3/2015 |
| WO | 2015/042438 A1 | 3/2015 |
| WO | 2015/054642 A2 | 4/2015 |
| WO | 2015/067108 A1 | 5/2015 |
| WO | 2015/177688 A1 | 11/2015 |
| WO | 2016/044694 A1 | 3/2016 |
| WO | 2016/097863 A1 | 6/2016 |
| WO | 2016/097870 A1 | 6/2016 |
| WO | 2016/170324 A1 | 10/2016 |

OTHER PUBLICATIONS

Debes et al., "p300 in Prostate Cancer Proliferation and Progression", Cancer Research, Nov. 15, 2003, vol. 63, pp. 7638-7640.

Denissen et al., "The Orally Active Renin Inhibitor A-74273, In Vivo and In Vitro Morpholine Ring Metabolism in Rats, Dogs, and Humans", Drug Metabolism and Disposition, 1994, vol. 22, No. 6, pp. 880-888.

Hay et al., "The design and synthesis of 5- and 6-isoxazolylbenzimidazoles as selective inhibitors of the BET bromodomains", Med. Chem. Commun., 2013, vol. 4, pp. 140-144.

Jones et al., "The Epigenomics of Cancer", Cell, Feb. 23, 2007, vol. 128, pp. 683-692.

Linja et al., "Expression of Androgen Receptor Coregulators in Prostate Cancer", Clinical Cancer Research, Feb. 1, 2004, vol. 10, pp. 1032-1040.

George S Mack, "To selectivity and beyond", Nature Biotechnology, Dec. 2010, vol. 28, No. 12, pp. 1259-1266.

Thong et al., "p300 Acetyltransferase Regulates Androgen Receptor Degradation and PTEN-Deficient Prostate Tumorigenesis", Cancer Research, Mar. 15, 2014, vol. 74, No. 6, pp. 1870-1880.

* cited by examiner

ISOXAZOLYL SUBSTITUTED IMIDAZOPYRIDINES

CROSS-REFERENCE TO RELATED APPLICATIONS

This application is a U.S. National Stage application of PCT/GB2016/051087 filed 20 Apr. 2016, which claims priority to Great Britain Application No. 1506660.8 filed 20 Apr. 2015, the entire disclosures of which are hereby incorporated by reference in their entireties.

FIELD OF THE INVENTION

The present invention relates to a series of novel isoxazolyl imidazopyridines and to their use as modulators of p300 and/or CBP activity.

BACKGROUND TO THE INVENTION

Genetic and epigenetic modifications are critical to all stages of cancer disease progression and epigenetic silencing has been shown to be important in the misregulation of genes involved in all of the hallmarks of cancer (Jones, P. A. and Baylin, S. B. (2007) "The epigenomics of cancer", *Cell*, Vol. 128, pp. 683-692). The underlying epigenetic modifications that mediate regulation include DNA methylation and post translational histone modification. The latter includes methylation, acetylation, and ubiquitination. DNA-demethylating agents and histone deacetylase inhibitors have shown anti-tumour activity and a number of agents have been approved for use in the treatment of haematological malignancies. The enzymes mediating histone modification, including histone acetyltransferases (HATs) which acetylate histone and non-histone proteins, represent a wave of second generation targets for small molecule drug intervention.

Prostate cancer is the most common malignancy, and the second leading cause of cancer mortality among men. The treatment for clinically localised disease is typically surgery or radiation therapy. For patients who recur systemically after definitive treatment, or who present with loco-regional or metastatic disease, long term disease control is the primary objective. Typically, this entails a series of hormonal therapies that suppress androgen receptor (AR) signalling, since prostate cancers are exquisitely dependent upon AR function for survival and progression. Although AR targeted therapies inhibit tumour growth, disease is rarely eliminated and resistance to therapy is acquired through restored AR function. Progression to this 'castration resistant' prostate cancer (CRPC) represents the lethal phenotype of the illness. It is estimated that between 50-60% of patients that develop metastatic disease have CRPC. Recently, several new therapeutic agents have been approved for the treatment of CRPC. These however, provide limited clinical efficacy and serve only to prolong progression. Novel and tolerable agents are therefore necessary to make further gains in the treatment of CRPC.

Multiple cellular mechanisms lead to the progression of CRPC. In all cases, acquisition of the CRPC phenotype is mediated via re-activation of the AR pathway. The acetyltransferase p300 directly regulates AR levels and AR signalling activity in prostate cancer cells (Zhong et al., 'p300 acetyltransferase regulates androgen-receptor degradation and PTEN-deficient prostate tumorigenesis,' *Cancer Res.*, Vol. 74, pp. 1870-1880, 2014). Therapeutic modulation of p300 activity would therefore target all known adaptive mechanisms which lead to the development of CRPC. Approved therapies and those in clinical studies primarily target only one or other of theses cellular mechanisms. The modulation of p300 activity directly provides an opportunity to more broadly modulate AR activity in CRPC than current and other experimental therapeutic strategies. In addition, resistance mechanisms to recently approved agents have been shown to be AR-dependent (Cai, C. et al., (2011) 'Intratumoral de novo steroid synthesis activates androgen receptor in castration-resistant prostate cancer and is up-regulated by treatment with Cyp17A1 inhibitors,' *Cancer Res.*, Vol. 71, pp. 6503-6513). Modulation of p300 should therefore inhibit resistance to current therapies and potentially provide improved and sustained efficacy and greater clinical utility.

In common with p300, the CREB (cyclic-AMP response element binding protein) binding protein (CBP) is an acetyltransferase that acts as a transcriptional co-activator in human cells. Both CBP and p300 possess a single bromodomain (BRD) and a lysine acetyltransferase (KAT) domain, which are involved in the post-translational modification and recruitment of histones and non-histone proteins. There is high sequence similarity between CBP and p300 in the conserved functional domains (see Duncan A. Hay et al, JACS 2014, 135, 9308-9319). Modulation of CBP activity therefore provides a promising route to the treatment of certain cancers. Accordingly, compounds that can modulate, e.g. inhibit, the activity of p300 and/or CBP are of interest in cancer therapy.

SUMMARY OF THE INVENTION

It has now been found that a series of novel compounds have activity in modulating p300 and/or CBP activity. The compounds therefore have potential utility in treating cancer, particularly prostate cancer.

Accordingly, the present invention provides a compound which is an isoxazolyl imidazopyridine of formula (I):

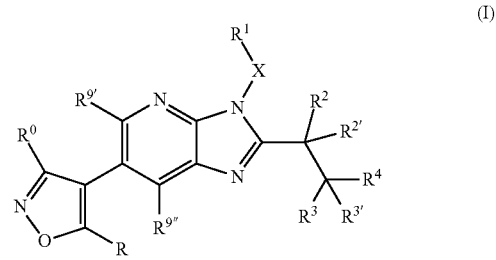

wherein
R⁰ and R, which are the same or different, are each H or $C_{1-6}$ alkyl;
$R^{9'}$ and $R^{9''}$, which are the same or different, are each H or F;
X is $-(alk)_n-$, $-alk-C(=O)-NR-$, $-alk-NR-C(=O)-$ or $-alk-C(=O)-$;
$R^1$ is selected from $-S(=O)_2R'$ and a 4- to 7-membered heterocyclic group which is unsubstituted or substituted;
$R^2$ and $R^{2'}$, which are the same or different, are each H or $C_{1-6}$ alkyl; or $R^2$ and $R^{2'}$ form, together with the C atom to which they are attached, a $C_{3-6}$ cycloalkyl group;
$R^3$ and $R^{3'}$, which are the same or different, are each H, $C_{1-6}$ alkyl, OH or F;

R⁴ is phenyl or a 5- to 12-membered N-containing heteroaryl group and is unsubstituted or substituted;

alk is $C_{1-6}$ alkylene;
R' is $C_{1-6}$ alkyl; and
n is 0 or 1;

or a pharmaceutically acceptable salt thereof.

In another aspect the invention provides a pharmaceutical composition comprising an isoxazolyl imidazopyridine of formula (I) as defined above or a pharmaceutically acceptable salt thereof and a pharmaceutically acceptable carrier. The pharmaceutical composition may further comprise one or more additional chemotherapeutic agents, for instance as mentioned below.

In a further aspect the invention provides an isoxazolyl imidazopyridine of formula (I) as defined above, or a pharmaceutically acceptable salt thereof, for use as a modulator of p300 activity.

DETAILED DESCRIPTION OF THE INVENTION

The term "substituted" includes the implicit provision that substitution be in accordance with the permitted valence of the substituted atom and the substituent and that the substitution results in a stable compound (i.e. one that does not spontaneously undergo transformation such as a rearrangement cyclisation, or elimination). In certain embodiments, a single atom may be substituted with more than one substituent as long as such substitution is in accordance with the permitted valence of the atom. In certain embodiments, a group that is substituted may be substituted by one substituent group or it may be multiply substituted on multiple carbon atoms. When any group defined herein is substituted, it is typically substituted by $R^{10}$ as defined below. The group may, for instance, be mono-, di- or tri-substituted by a group $R^{10}$ as defined below.

In certain of the isoxazolyl imidazopyridines of formula (I), dependant on the nature of the substituent, there may be chiral carbon atoms and therefore the compounds may exist as stereoisomers. The invention extends to all optical isomers such as stereoisomeric forms of the compounds of formula (I), including enantiomers, diastereomers and mixtures thereof, such as racemates. The different stereoisomeric forms may be separated or resolved one from the other by conventional methods or any given isomer may be obtained by conventional stereoselective or stereospecific syntheses.

The compounds of the invention can exist in various tautomeric forms and it is to be understood that the invention encompasses all such tautomeric forms.

It is understood that certain compounds of the invention contain both acidic and basic groups and may therefore exist as zwitterions at certain pH values.

As used herein, the terms "treat" and "treatment" refer to both therapeutic treatment and prophylactic or preventative measures, wherein the object is to prevent or slow down (lessen) an undesired physiological change or disorder, such as the development or spread of cancer. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "pharmaceutically acceptable" indicates that the substance or composition must be compatible chemically and/or toxicologically with the other ingredients comprising a formulation, and/or the patient being treated therewith.

A $C_{1-6}$ alkyl group or moiety is linear or branched. A $C_{1-6}$ alkyl group is typically a $C_{1-4}$ alkyl group, or a $C_{1-2}$ alkyl group. Examples of $C_{1-6}$ alkyl groups and moieties include methyl, ethyl, n-propyl, i-propyl, n-butyl, i-butyl, t-butyl, n-pentyl, i-pentyl (i.e. 3-methylbut-1-yl), t-pentyl (i.e. 2-methylbut-2-yl), neopentyl (i.e. 2,2-dimethylpropan-1-yl), n-hexyl, i-hexyl (i.e. 4-methylpentan-1-yl), t-hexyl (i.e. 3-methylpentan-3-yl) and neopentyl (i.e. 3,3-dimethylbutan-1-yl). Typically a $C_{1-6}$ alkyl group is methyl (Me). For the avoidance of doubt, where two alkyl moieties are present in a group, the alkyl moieties may be the same or different. A $C_{1-6}$ alkyl group is unsubstituted or substituted, typically by one or more groups $R^{10}$ as defined below. For example, a $C_{1-6}$ alkyl group is unsubstituted or substituted by 1, 2 or 3 groups $R^{10}$ as defined below.

A $C_{1-6}$ alkylene group or moiety is an unsubstituted or substituted, linear or branched, saturated divalent aliphatic hydrocarbon group or moiety containing 1 to 6 carbon atoms. Typically it is a $C_{1-3}$ alkylene group or moiety. Examples include methylene, ethylene, n-propylene and i-propylene groups and moieties. More typically it is methylene or ethylene. When the alkylene group is substituted it is typically substituted by a group $R^{10}$ as defined below.

A $C_{3-6}$ cycloalkyl group or moiety is a saturated monovalent hydrocarbon ring having 3 to 6 carbon atoms. It is thus a 3-, 4-, 5- or 6-membered carbocyclic ring containing only saturated bonds. Examples of a cycloalkyl group include cyclopropyl, cyclobutyl, cyclopentyl and cyclohexyl. In one embodiment a cycloalkyl group is cyclopropyl.

A 5- to 12-membered N-containing heteroaryl group or moiety is a monovalent 5- to 12-membered aromatic heterocyclic group which contains 1, 2, 3, or 4 nitrogen atoms, typically 1 or 2 N atoms. It is linked via one of its ring C or N atoms and is monocyclic or bicyclic. In one embodiment it is C-linked. In another embodiment it is N-linked. It may be, for example, a 5- to 7-membered N-containing monocyclic heteroaryl group, for instance a 5- or 6-membered N-containing heteroaryl group. Examples of a 5- to 12-membered, C-linked, N-containing heteroaryl group include pyrrolyl, imidazolyl, pyridyl, pyrazinyl, pyrimidinyl, quinolyl, isoquinolyl, quinazolinyl, quinoxalinyl, indolyl, isoindolyl, indazolyl, pyrrolopyridinyl and pyrrolopyrimidinyl groups. When substituted, a 5- to 12-membered N-containing heteroaryl group is typically substituted by one or more, e.g. 1, 2 or 3, groups selected from unsubstituted $C_{1-4}$ alkyl and a group $R^{11}$ as defined below In one embodiment a 5- to 12-membered N-containing heteroaryl group is unsubstituted.

A 4- to 7-membered heterocyclic group is a saturated monovalent 4-, 5-, 6- or 7-membered heterocyclic ring containing at least one heteroatom selected from O, N and S. It may be, for instance, a 4- to 6-membered heterocyclic group. It is linked via one of its ring C atoms or via a ring heteroatom. In one embodiment it is C-linked. In another embodiment it is N-linked. Examples of a 4- to 7-membered heterocyclic group include oxetane, thietane, azetidine, pyrrolidine, piperidine, piperazine, tetrahydropyran, tetrahydrothiopyran, morpholine and the following N-linked spiro group:

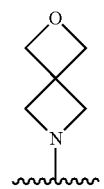 [SMILES: *N1CC2(COC2)C1]

A 4- to 7-membered heterocyclic group is unsubstituted or substituted, typically by a group $R^{10}$ as defined below. It may be substituted on a ring carbon atom or on a ring heteroatom, as permitted by the valency of the atom.

A halogen or halo group is F, Cl, Br or I. Typically it is F, Cl or Br, more typically F.

A $C_{1-6}$ alkoxy group is linear or branched. It is typically a $C_{1-4}$ alkoxy group, for example a methoxy, ethoxy, propoxy, i-propoxy, n-propoxy, n-butoxy, sec-butoxy or tert-butoxy group. A $C_{1-6}$ alkoxy group is unsubstituted or substituted, typically by one or more groups $R^{10}$ as defined below.

When in formula (I) n=0, moiety -(alk)$_n$- is absent and X is thus a direct bond. X is typically selected from a direct bond, —CH$_2$—, —CH$_2$CH$_2$—, —CH$_2$CH$_2$CH$_2$—, —CH$_2$—C(=O)—NMe-, —CH$_2$—C(=O)—NH— and —CH$_2$—C(=O)—.

When $R^1$ is a 4- to 7-membered heterocyclic group it is typically a morpholinyl, thiomorpholinyl, piperidinyl, piperazinyl, pyrrolidinyl, tetrahydropyranyl, oxetanyl, tetrahydrothiopyranyl or tetrahydrofuranyl group, or an N-linked spiro group having the structure shown above. It is unsubstituted or substituted, for instance by a group $R^{10}$ as defined below.

When $R^4$ is a 5- to 12-membered N-containing heteroaryl group it is typically selected from pyrrolyl, imidazolyl, pyridyl, pyrazinyl, pyrimidinyl, quinolyl, isoquinolyl, quinazolinyl, quinoxalinyl, indolyl, isoindolyl, indazolyl, pyrrolopyridinyl and pyrrolopyrimidinyl. More typically it is selected from pyridyl, pyrimidinyl, quinolyl, isoquinolyl, quinoxalinyl, pyrrolopyridinyl and indolyl.

$R^4$ is unsubstituted or substituted. When substituted it may be mono-, di- or tri-substituted, for instance by a group $R^{11}$ as defined below.

$R^{9'}$ and $R^{9'''}$ are each H or F. Typically $R^{9'}$ is H and $R^{9'''}$ is H or F, more preferably H.

$R^{10}$ is selected from unsubstituted $C_{1-6}$ alkyl, $C_{3-6}$ cycloalkyl, halo, OH, $C_{1-6}$ alkoxy, —C(O)R", —C(O)$_2$R", —C(O)NR"$_2$, oxo (=O), dioxo, —CH$_2$OR", —S(O)$_m$R", —NR"C(O) R", —S(O)$_m$NR"$_2$, and CF$_3$, wherein m is 1 or 2 and each R" is independently selected from H and unsubstituted $C_{1-6}$ alkyl. Typically $R^{10}$ is selected from unsubstituted $C_{1-6}$ alkyl, halo, OH, $C_{1-6}$ alkoxy, —C(O)R", —C(O) NR"$_2$, oxo (=O) and dioxo.

$R^{11}$ is selected from unsubstituted $C_{1-6}$ alkyl, halo, —OH, $C_{1-6}$ alkoxy, —CN, —OCHF$_2$, —OCF$_3$, —C(O)R", —C(O)$_2$R", —C(O)NR"$_2$, —CH$_2$OR", —S(O)$_m$R" and —S(O)$_m$NR"2 wherein m and R" are as defined above.

In one preferred embodiment, the isoxazolyl imidazopyridine of the invention has the following formula (Ia):

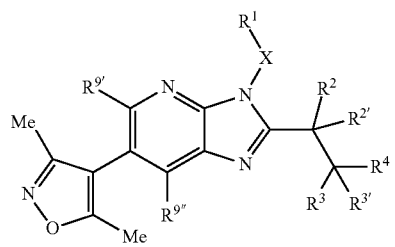

(Ia)

wherein each of $R^{9'}$, $R^{9'''}$, X, $R^1$, $R^2$, $R^{2'}$, $R^3$, $R^{3'}$ and $R^4$ is as defined above for formula (I).

In another preferred embodiment of the invention, the isoxazolyl imidazopyridine has the following formula (Ib):

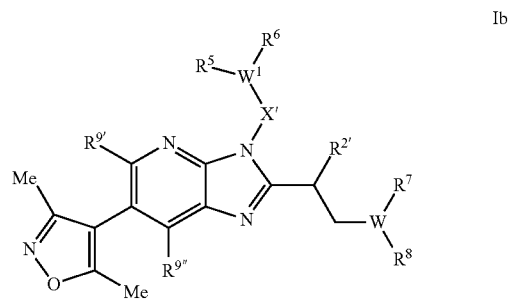

Ib wherein:

$R^{9'}$ and $R^{9'''}$ are as defined above for formula (I);

W is N or C;

$W^1$ is N or CH;

X' is $C_{1-3}$ alkylene or —(CH$_2$)—C(=O)—NH—;

$R^2$ is H, Me or Et;

$R^5$ is H and $R^6$ is —S(=O)$_2$Me, or $R^5$ and $R^6$ form, together with the atom of $W^1$ to which they are attached, a heterocyclic group selected from pyrrolidinyl, thiopyranyl, pyranyl and piperidinyl, which group is unsubstituted or substituted; and $R^7$ and $R^8$ form, together with the C or N atom to which they are attached, a group selected from phenyl, pyridinyl, pyrimidinyl, quinolinyl, isoquinolinyl, pyrrolopyridinyl and quinoxalinyl, which group is unsubstituted or substituted.

In one aspect of the invention, the moiety represented in formulae (I) and (Ia) as —X—$R^1$ and in formula (Ib) as

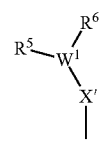

is selected from the following structures:

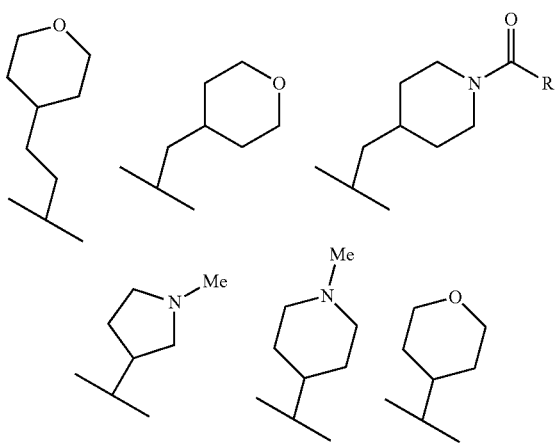

-continued

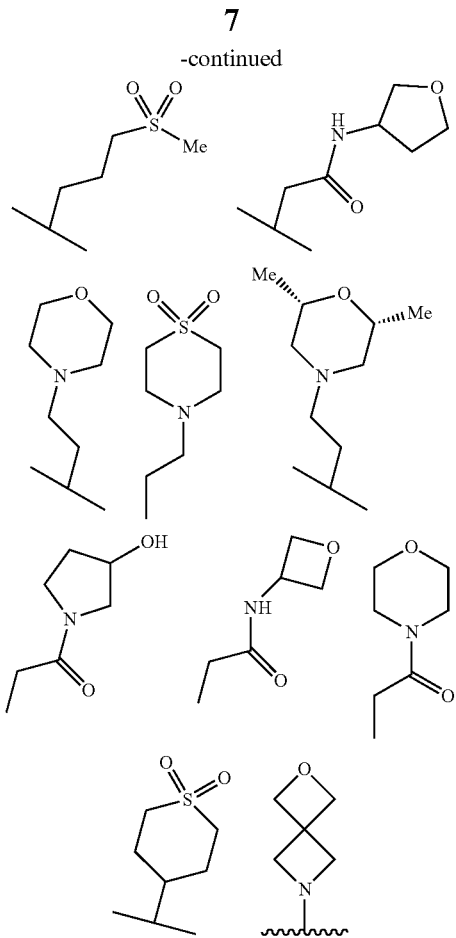

In another aspect of the invention the moiety represented in formula (I) and (Ia) as

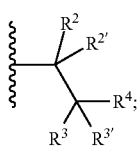

and in formula (Ib) as

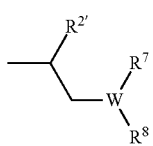

is represented by one of the following structures:

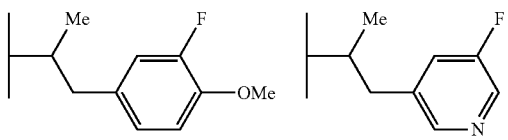

-continued

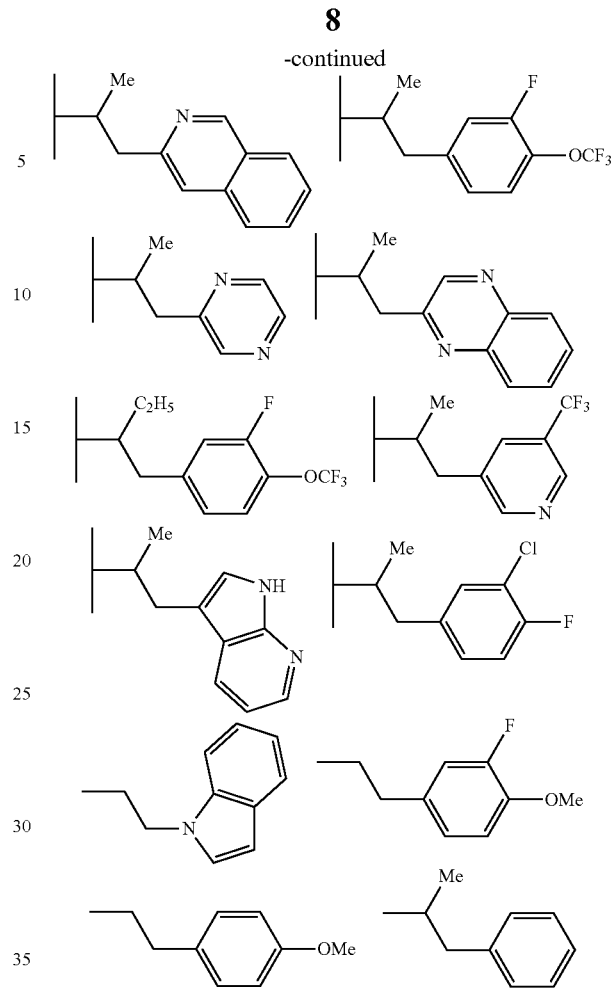

More typically it is represented by one of the following structures:

In formula (I) as defined above, each of $R^0$ and $R$ is independently H or $C_{1-6}$ alkyl. Thus, for instance, $R^0$ is H and $R$ is $C_{1-6}$ alkyl; $R$ is H and $R^0$ is $C_{1-6}$ alkyl; each of $R^0$ and $R$ is H; or each of $R^0$ and $R$ is $C_{1-6}$ alkyl. In each of these variants $C_{1-6}$ alkyl is typically methyl or ethyl, preferably methyl.

In formulae (I) and (Ia) as defined above, each of $R^2$ and $R^{2'}$ is independently H or $C_{1-6}$ alkyl. For instance, $R^2$ is H and $R^{2'}$ is $C_{1-6}$ alkyl; $R^{2'}$ is H and $R^2$ is $C_{1-6}$ alkyl; $R^2$ and $R^{2'}$ are both H; or $R^2$ and $R^{2'}$ are both $C_{1-6}$ alkyl. In each of these variants $C_{1-6}$ alkyl is typically methyl or ethyl, preferably methyl. Alternatively $R^2$ and $R^{2'}$ form, together with the C atom to which they are attached, a $C_{3-6}$ cycloalkyl group such as cyclopropyl.

In one variant of formulae (I), (Ia) and (Ib) as defined above, each of $R^{9'}$ and $R^{9'''}$ is H. In another variant, one of $R^{9'}$ and $R^{9'''}$ is F and the other is H. In a third variant, each of $R^{9'}$ and $R^{9'''}$ is F.

Compounds of the invention may contain asymmetric or chiral centres and thus exist in different stereoisomeric forms. The structural formulae above encompass all stereoisomeric forms of the compounds of the invention including diastereomers, enantiomers and racemic mixtures. Diastereomers and enantiomers may be obtained by stereoselective synthetic strategies, for instance via enantiomeric synthesis.

Specific examples of compounds of the invention include those listed in the following table:

| # | Structure | Name |
|---|---|---|
| 1 | 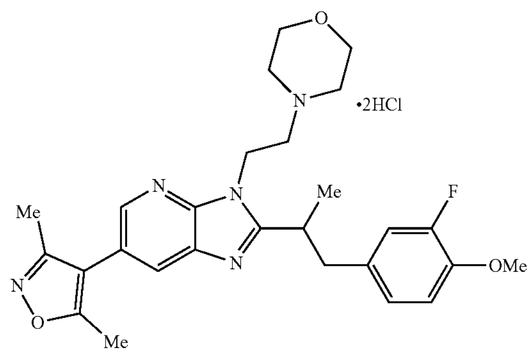 [SMILES: COc1ccc(CC(C)c2nc3cc(-c4c(C)noc4C)cnc3n2CCN2CCOCC2)cc1F] | 4-(2-(6-(3,5-dimethylisoxazol-4-yl)-2-(1-(3-fluoro-4-methoxyphenyl)propan-2-yl)-3H-imidazo[4,5-b]pyridin-3-yl)ethyl)morpholine bis hydrochloride |
| 2 | 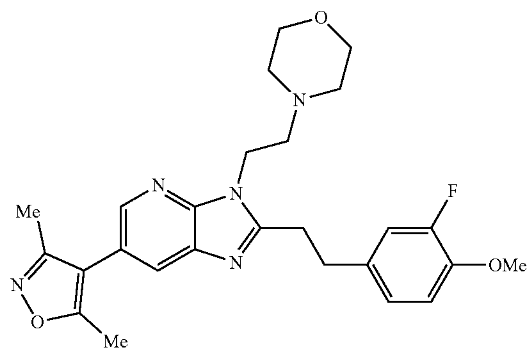 [SMILES: COc1ccc(CCc2nc3cc(-c4c(C)noc4C)cnc3n2CCN2CCOCC2)cc1F] | 4-(2-(6-(3,5-dimethylisoxazol-4-yl)-2-(3-fluoro-4-methoxyphenethyl)-3H-imidazo[4,5-b]pyridin-3-yl)ethyl)morpholine |
| 3 | 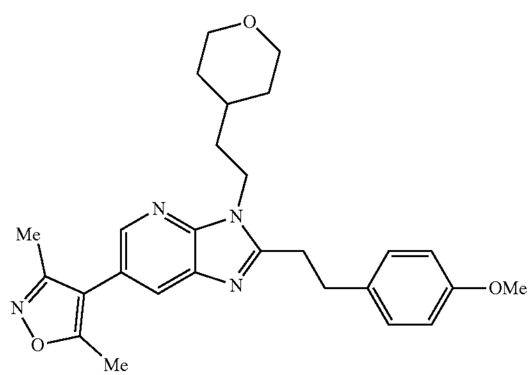 [SMILES: COc1ccc(CCc2nc3cc(-c4c(C)noc4C)cnc3n2CCC2CCOCC2)cc1] | 4-(2-(4-methoxyphenethyl)-3-(2-(tetrahydro-2H-pyran-4-yl)ethyl)-3H-imidazo[4,5-b]pyridin-6-yl)-3,5-dimethylisoxazole |
| 4 | 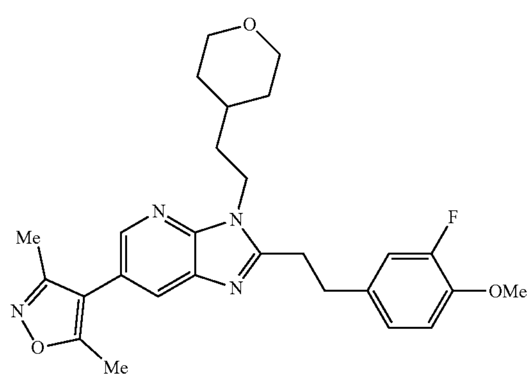 [SMILES: COc1ccc(CCc2nc3cc(-c4c(C)noc4C)cnc3n2CCC2CCOCC2)cc1F] | 4-(2-(3-fluoro-4-methoxyphenethyl)-3-(2-(tetrahydro-2H-pyran-4-yl)ethyl)-3H-imidazo[4,5-b]pyridin-6-yl)-3,5-dimethylisoxazole |

| | | |
|---|---|---|
| 5 | 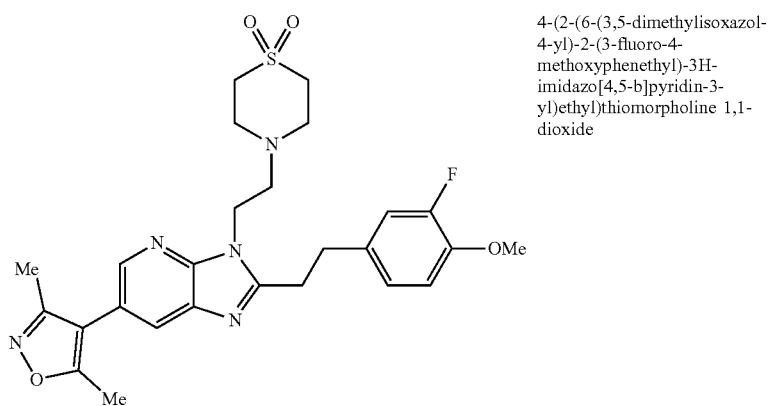 | 4-(2-(6-(3,5-dimethylisoxazol-4-yl)-2-(3-fluoro-4-methoxyphenethyl)-3H-imidazo[4,5-b]pyridin-3-yl)ethyl)thiomorpholine 1,1-dioxide |
| 6 | 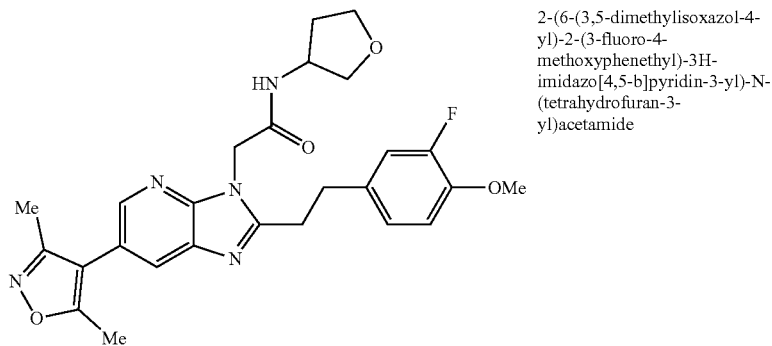 | 2-(6-(3,5-dimethylisoxazol-4-yl)-2-(3-fluoro-4-methoxyphenethyl)-3H-imidazo[4,5-b]pyridin-3-yl)-N-(tetrahydrofuran-3-yl)acetamide |
| 7 | 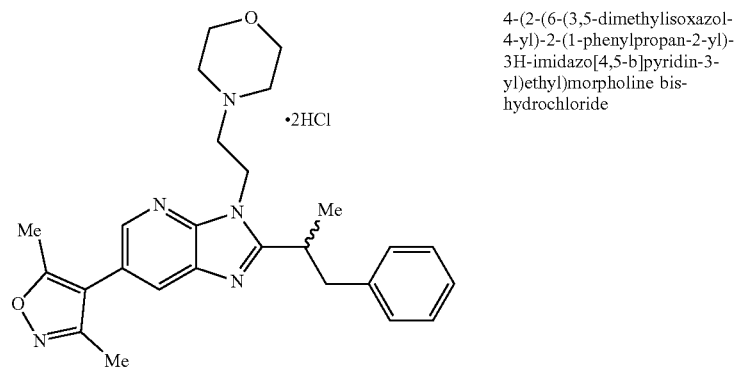 | 4-(2-(6-(3,5-dimethylisoxazol-4-yl)-2-(1-phenylpropan-2-yl)-3H-imidazo[4,5-b]pyridin-3-yl)ethyl)morpholine bis-hydrochloride |
| 8 | 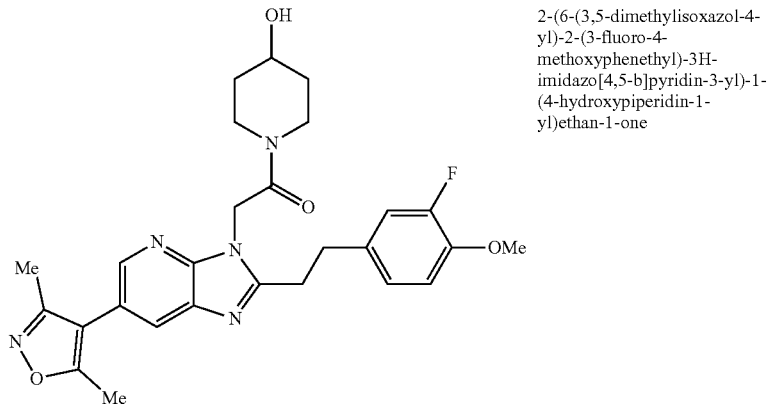 | 2-(6-(3,5-dimethylisoxazol-4-yl)-2-(3-fluoro-4-methoxyphenethyl)-3H-imidazo[4,5-b]pyridin-3-yl)-1-(4-hydroxypiperidin-1-yl)ethan-1-one |

-continued

| | | |
|---|---|---|
| 9 | 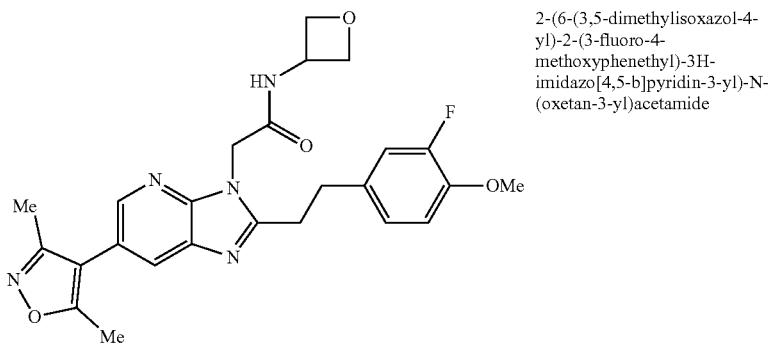 | 2-(6-(3,5-dimethylisoxazol-4-yl)-2-(3-fluoro-4-methoxyphenethyl)-3H-imidazo[4,5-b]pyridin-3-yl)-N-(oxetan-3-yl)acetamide |
| 10 | 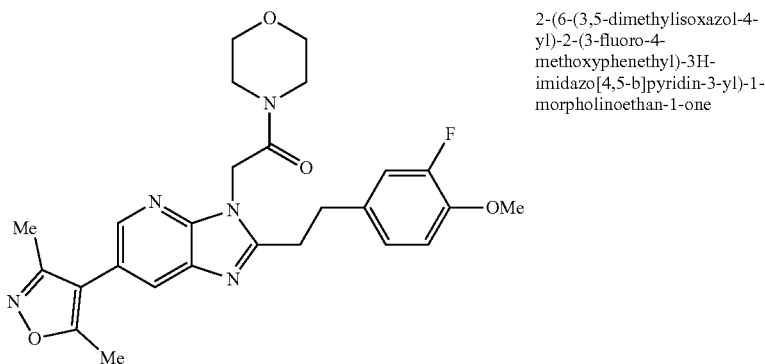 | 2-(6-(3,5-dimethylisoxazol-4-yl)-2-(3-fluoro-4-methoxyphenethyl)-3H-imidazo[4,5-b]pyridin-3-yl)-1-morpholinoethan-1-one |
| 11 | 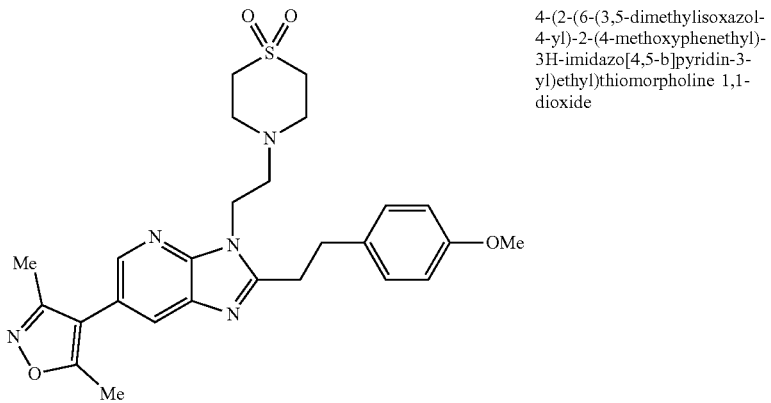 | 4-(2-(6-(3,5-dimethylisoxazol-4-yl)-2-(4-methoxyphenethyl)-3H-imidazo[4,5-b]pyridin-3-yl)ethyl)thiomorpholine 1,1-dioxide |
| 12 | 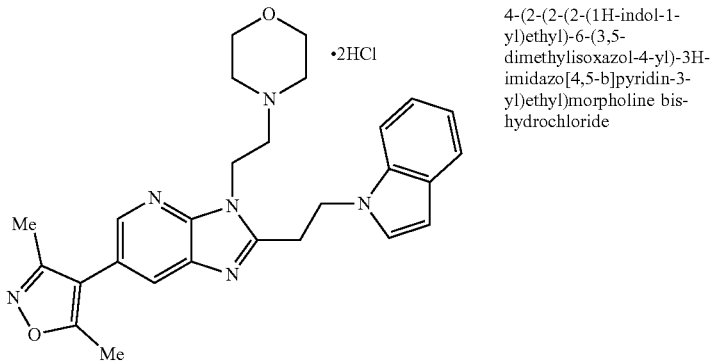 | 4-(2-(2-(2-(1H-indol-1-yl)ethyl)-6-(3,5-dimethylisoxazol-4-yl)-3H-imidazo[4,5-b]pyridin-3-yl)ethyl)morpholine bis-hydrochloride |

| | | |
|---|---|---|
| 13 | 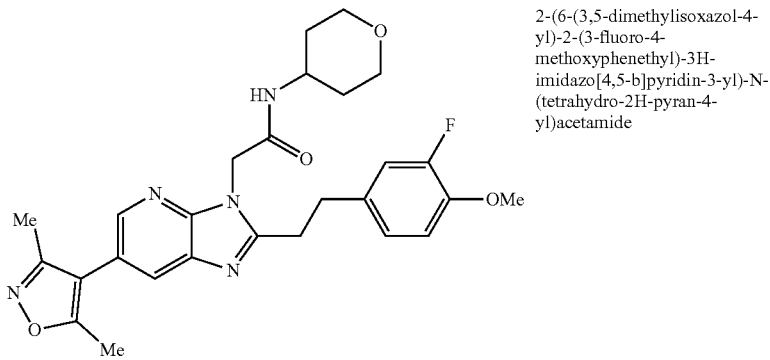 | 2-(6-(3,5-dimethylisoxazol-4-yl)-2-(3-fluoro-4-methoxyphenethyl)-3H-imidazo[4,5-b]pyridin-3-yl)-N-(tetrahydro-2H-pyran-4-yl)acetamide |
| 14 | 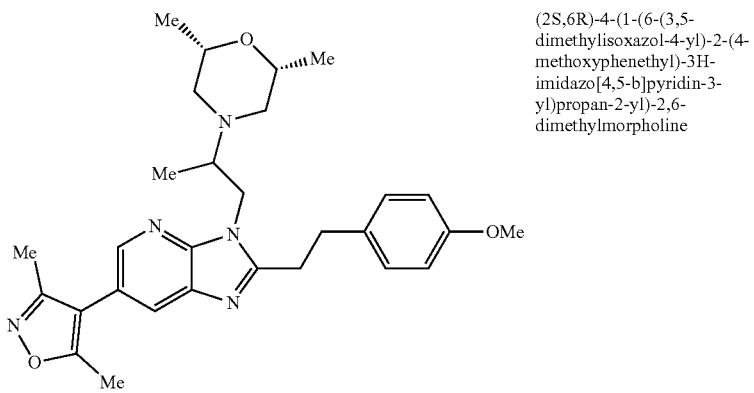 | (2S,6R)-4-(1-(6-(3,5-dimethylisoxazol-4-yl)-2-(4-methoxyphenethyl)-3H-imidazo[4,5-b]pyridin-3-yl)propan-2-yl)-2,6-dimethylmorpholine |
| 15 | 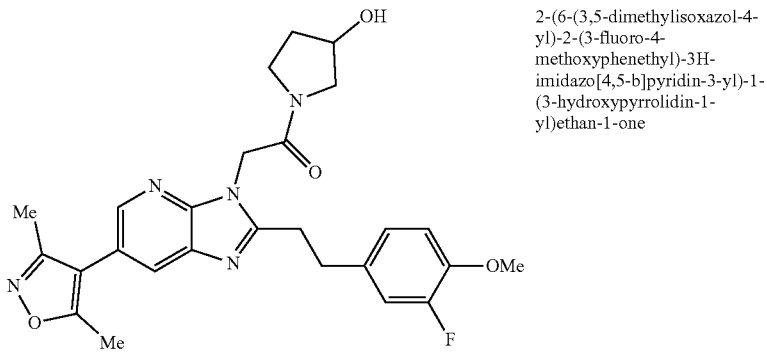 | 2-(6-(3,5-dimethylisoxazol-4-yl)-2-(3-fluoro-4-methoxyphenethyl)-3H-imidazo[4,5-b]pyridin-3-yl)-1-(3-hydroxypyrrolidin-1-yl)ethan-1-one | and the pharmaceutically acceptable salts thereof.

A compound of the invention may be prepared by a process which comprises treating a compound of formula (II):

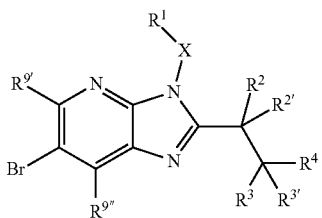

wherein each of $R^1$, $R^2$, $R^{2'}$, $R^3$, $R^{3'}$, $R^4$, $R^{9'}$ and $R^{9''}$ is as defined above for formula (I), with a boronic acid of formula (III):

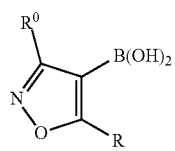

in which each of $R^0$ and R is as defined above for formula (I), in the presence of $Pd(PPh_3)_4$ and $Na_2CO_3$ in aqueous ethanol. The aqueous ethanol is typically 30-70% EtOH/water.

The scheme shown below illustrates a specific synthetic strategy by which compounds of the invention may be produced.

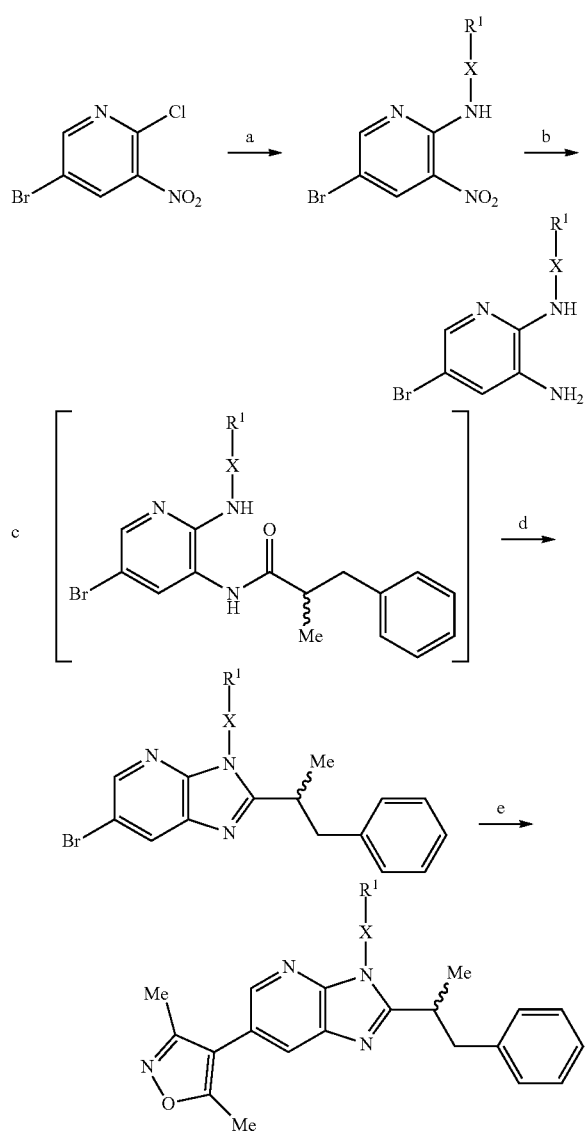

a. R₁——NH₂, TEA, THF, rt or R₁——NH₂·HCl, TEA, DMF, 70-90° C. -60-90%
b. Na₂S₂O₄, THF/H₂O, NH₄OH or Fe, AcOH or Fe, NH₄Cl, EtOH/H₂O, 80° C. -30-80%
c. HATU, hydrocinnamic acid, TEA, DCM or DMF -50-90% (either purified or used crude)
d. AcOH, 60-100° C. or HCl/1,4-dioxane -20-90%
e. Dimethylisoxazoleboronic acid, Na₂CO₃, Pd(PPh₃)₄, EtOH/water -30-70%

A key to the abbreviations used in the above schemes is provided in the Examples section below.

An isoxazolyl imidazopyridine of formula (I) may be converted into a pharmaceutically acceptable salt, and salts may be converted into the free compound, by conventional methods. Pharmaceutically acceptable salts include salts of inorganic acids such as hydrochloric acid, hydrobromic acid and sulfuric acid, and salts of organic acids such as acetic acid, oxalic acid, malic acid, methanesulfonic acid, trifluoroacetic acid, benzoic acid, citric acid and tartaric acid. In the case of compounds bearing a free carboxy substituent, the salts include both the above-mentioned acid addition salts and the salts of sodium, potassium, calcium and ammonium. The latter are prepared by treating the free benzimidazolyl isoxazole of formula (I), or an acid addition salt thereof, with the corresponding metal base or ammonia.

An isoxazolyl imidazopyridine of formula (I) or a pharmaceutically acceptable salt thereof is hereafter referred to as a compound of the invention. Compounds of the invention have been found in biological tests to bind to the histone acetyltransferase (HAT), p300, as described in Example 16 below.

p300 is a transcriptional coactivator involved in the regulation of multiple biological processes; proliferation, apoptosis, cell cycle regulation and DNA damage response. p300 primarily functions as a transcription cofactor for a number of oncoproteins including Jun, Fos and E2F. In addition, it acts as a histone acetyltransferase and can also acetylate multiple non-histone proteins such as p53, p73, and Rb. p300 has been reported to act as a tumour suppressor or as an oncoprotein dependent upon the nature of the cancer. Multiple studies have shown that p300 expression correlates with disease progression and decreased survival.

p300 is up-regulated in human prostate cancer progression and has been shown to be an AR co-activator (Debes, J. D., et al., (2003) 'p300 in prostate cancer proliferation and progression,' *Cancer Res.*, Vol. 63, pp. 7638-7640; and Linja, M. J. et al., (2004) 'Expression of androgen receptor coregulators in prostate cancer,' *Clin. Cancer Res.*, Vol. 10, pp. 1032-1040).

p300 has recently been shown to directly regulate AR protein degradation (Zhong et al., 2014). p300 mediated AR acetylation was shown to inhibit AR ubiquitination and subsequent AR proteasome degradation (Zhong et al., 2014, cited above). The direct inhibition of p300 activity would therefore promote AR degradation.

Given the high molecular heterogeneity of prostate cancer, the identification of appropriate biomarkers is critical to the effective positioning and evaluation of targeted small molecule therapies. It is proposed that markers of the development of the CRPC phenotype via AR resurgence are used for patient stratification for the evaluation of p300 modulators. These include PSA and circulating tumour cell (CTC) counts. In terms of biomarkers to enable the monitoring of the modulation of p300 activity, direct readouts include; determination of the AR and AR splice variant levels; modulation of AR activity by assessing levels of AR responsive genes including PSA, TMPRSS2 and KLK2. Other surrogate markers of AR functional activity include p21, c-Myc and p53. Given that multiple therapeutic agents which modulate AR activity are approved for use in CRPC, biomarkers to assess effects of p300 targeting and subsequent AR modulation are already widely available and used in clinical settings.

Various types of cancer have been shown to express AR. In addition to prostate cancer, these include breast and bladder cancer. Modulation of p300 activity would be expected to have therapeutic utility in the treatment of such cancers and other indications in which AR is expressed. In addition, it is feasible that p300 regulates the levels of other nuclear hormone receptors, thereby further expanding the clinical utility of p300 targeted agents.

A compound of the invention has activity as a modulator of p300 and/or CBP activity. It may therefore be used to treat cancer, or another clinical condition in which AR is expressed. The cancers that can be treated are those which express AR, or which are otherwise associated with AR. These cancers include prostate cancer, breast cancer and bladder cancer. The prostate cancer may be, for instance, castration-resistant prostate cancer (CRPC). A human or animal patient suffering from cancer may thus be treated by a method comprising the administration thereto of a compound of the invention. The condition of the patient may thereby be improved or ameliorated.

A compound of the invention may thus be administered to a human or animal patient in conjunction with radiotherapy or another chemotherapeutic agent for the treatment of cancer. The present invention therefore further provides a combination therapy wherein a compound of the invention, or a pharmaceutical composition comprising a compound of the invention, is administered concurrently or sequentially with radiotherapy; or is administered concurrently sequentially or as a combined preparation with another chemotherapeutic agent or agents, for the treatment of cancer.

The or each other chemotherapeutic agent will be an agent conventionally used for the type of cancer being treated. Classes of chemotherapeutic agents with which a compound of the invention would typically be combined for the treatment of prostate cancer include androgen receptor antagonists, for instance Enzalutamide, and inhibitors of CYP17A1 (17α-hydroxylase/C17,20 lyase), for instance Abiraterone. Other chemotherapeutic agents with which a compound of the invention could be administered in combination therapy include Docetaxel.

The term "combination" as used herein refers to simultaneous, separate or sequential administration. Where the administration is sequential or separate, the delay in administering the second component should not be such as to lose the beneficial effect of the combination.

The present invention further provides a product comprising
(a) a compound of the invention as defined above; and
(b) a chemotherapeutic agent;
for separate, simultaneous or sequential administration in the prophylactic or therapeutic treatment of cancer, for instance the specific types of cancer mentioned above. The chemotherapeutic agent may be, for instance, an androgen receptor antagonist or an inhibitor of CYP17A1. More specifically, it may Enzalutamide or Abiraterone.

A compound of the invention can be administered in a variety of dosage forms, for example orally such as in the form of tablets, capsules, sugar- or film-coated tablets, liquid solutions or suspensions or parenterally, for example intramuscularly, intravenously or subcutaneously. The compound may therefore be given by injection or infusion.

The dosage depends on a variety of factors including the age, weight and condition of the patient and the route of administration. Daily dosages can vary within wide limits and will be adjusted to the individual requirements in each particular case.

Typically, however, the dosage adopted for each route of administration when a compound is administered alone to adult humans is 0.0001 to 50 mg/kg, most commonly in the range of 0.001 to 10 mg/kg, body weight, for instance 0.01 to 1 mg/kg. Such a dosage may be given, for example, from 1 to 5 times daily. For intravenous injection a suitable daily dose is from 0.0001 to 1 mg/kg body weight, preferably from 0.0001 to 0.1 mg/kg body weight. A daily dosage can be administered as a single dosage or according to a divided dose schedule.

A compound of the invention is formulated for use as a pharmaceutical or veterinary composition also comprising a pharmaceutically or veterinarily acceptable carrier or diluent. The compositions are typically prepared following conventional methods and are administered in a pharmaceutically or veterinarily suitable form. The compound may be administered in any conventional form, for instance as follows:

A) Orally, for example, as tablets, coated tablets, dragees, troches, lozenges, aqueous or oily suspensions, liquid solutions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations.

Tablets contain the active ingredient in admixture with non-toxic pharmaceutically acceptable excipients which are suitable for the manufacture of tablets. These excipients may be for example, inert diluents, such as calcium carbonate, sodium carbonate, lactose, dextrose, saccharose, cellulose, corn starch, potato starch, calcium phosphate or sodium phosphate; granulating and disintegrating agents, for example, maize starch, alginic acid, alginates or sodium starch glycolate; binding agents, for example starch, gelatin or acacia; lubricating agents, for example silica, magnesium or calcium stearate, stearic acid or talc; effervescing mixtures; dyestuffs, sweeteners, wetting agents such as lecithin, polysorbates or lauryl sulphate. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. Such preparations may be manufactured in a known manner, for example by means of mixing, granulating, tableting, sugar coating or film coating processes.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is present as such, or mixed with water or an oil medium, for example, peanut oil, liquid paraffin, or olive oil.

Aqueous suspensions contain the active materials in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinylpyrrolidone gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides for example polyoxyethylene sorbitan monooleate.

The said aqueous suspensions may also contain one or more preservatives, for example, ethyl or n-propyl p-hydroxybenzoate, one or more colouring agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents, such as those set forth above, and flavouring agents may be added to provide a palatable oral preparation. These compositions may be preserved by this addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally occurring phosphatides, for example soy bean lecithin, and esters or partial esters derived from fatty acids an hexitol anhydrides, for example sorbitan monooleate, and condensation products of the said partial esters with ethylene oxide, for example polyoxyethylene sorbitan monooleate. The emulsion may also contain sweetening and flavouring agents. Syrups and elixirs may be formulated with sweetening agents, for example glycerol, sorbitol or sucrose. In particular a syrup for diabetic patients can contain as carriers only products, for example sorbitol, which do not metabolise to glucose or which only metabolise a very small amount to glucose.

Such formulations may also contain a demulcent, a preservative and flavouring and coloring agents.

B) Parenterally, either subcutaneously, or intravenously, or intramuscularly, or intrasternally, or by infusion techniques, in the form of sterile injectable aqueous or oleaginous suspensions. This suspension may be formulated according to the known art using those suitable dispersing of wetting agents and suspending agents which have been mentioned above. The sterile injectable preparation may also be a sterile injectable solution or suspension in a non-toxic paternally-acceptable diluent or solvent, for example as a solution in 1,3-butane diol.

Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition fatty acids such as oleic acid find use in the preparation of injectables.

C) By inhalation, in the form of aerosols or solutions for nebulizers.

D) Rectally, in the form of suppositories prepared by mixing the drug with a suitable non-irritating excipient which is solid at ordinary temperature but liquid at the rectal temperature and will therefore melt in the rectum to release the drug. Such materials are cocoa butter and poly-ethylene glycols.

E) Topically, in the form of creams, ointments, jellies, collyriums, solutions or suspensions.

The invention will be further described in the Examples which follow:

EXAMPLES

Abbreviations
AcOH glacial acetic acid
aq aqueous
Ac acetyl
Boc tert-butoxycarbonyl
br broad
CatCart® catalytic cartridge
CDI 1,1-carbonyl-diimidazole
d doublet
DCM Dichloromethane
DIPEA N,N-diisopropylethylamine
DMF N,N-dimethylformamide
DMSO dimethyl sulfoxide
(ES$^+$) electrospray ionization, positive mode
Et Ethyl
EtOAc ethyl acetate
FCS foetal calf serum
HOBt 1-hydroxybenzotriazole
hr hour(s)
(M+H)$^+$ protonated molecular ion
Me methyl
MeCN acetonitrile
MeOH methanol
MHz megahertz
min minute(s)
m/z: mass-to-charge ratio
NMP 1-methylpyrrolidin-2-one (N-methyl-2-pyrrolidone)
NMR nuclear magnetic resonance (spectroscopy)
Ph phenyl
PBS phosphate buffered saline
PPh$_3$ triphenylphosphine
q quartet
RT room temperature
RP HPLC reverse phase high performance liquid chromatography
s singlet
SCX solid supported cation exchange (resin)
S$_N$Ar nucleophilic aromatic substitution
t triplet
TBAF tetrabutylammonium fluoride
TEA triethylamine
TFA trifluoroacetic acid
THF tetrahydrofuran
TIPS-Cl chlorotriisopropylsilane
TMB 3,3',5,5'-tetramethylbenzidine
XantPhos 4,5-bis(diphenylphosphino)-9,9-dimethylxanthene
HATU N-[(Dimethylamino)-1H-1,2,3-triazolo-[4,5-b]pyridin-1-ylmethylene]-N-methylmethanaminium hexafluorophosphate N-oxide General Procedures All starting materials and solvents were either obtained from commercial sources or prepared according to the literature citation. Unless otherwise stated all reactions were stirred. Organic solutions were routinely dried over anhydrous magnesium sulfate. Hydrogenations were performed on a Thales H-cube flow reactor under the conditions stated.

Column chromatography was performed on pre-packed silica (230-400 mesh, 40-63 μM) cartridges using the amount indicated. SCX was purchased from Supelco and treated with 1M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 1% NH₃ in MeOH.

Analytical Methods

Reverse Phase High Performance Liquid Chromatography: Analytical HPLC was carried out using a Waters Xselect CSH C18, 2.5 μm, 4.6×30 mm column eluting with a gradient of 0.1% Formic Acid in MeCN in 0.1% aqueous Formic Acid; a Waters Xbridge BEH C18, 2.5 μm, 4.6×30 mm column eluting with a gradient of MeCN in aqueous 10 mM Ammonium Bicarbonate. UV spectra of the eluted peaks were measured using either a diode array or variable wavelength detector on an Agilent 1100 system.

Analytical LCMS was carried out using a Waters Xselect CSH C18, 2.5 μm, 4.6×30 mm column eluting with a gradient of 0.1% Formic Acid in MeCN in 0.1% aqueous Formic Acid (Method 1); a Waters Xbridge BEH C18, 2.5 μm, 4.6×30 mm column eluting with a gradient of MeCN in aqueous 10 mM Ammonium Bicarbonate (Method 2). UV and mass spectra of the eluted peaks were measured using a variable wavelength detector on either an Agilent 1200 with or an Agilent Infinity 1260 LCMS with 6120 single quadrupole mass spectrometer with positive and negative ion electrospray.

Preparative HPLC was carried out using a Waters Xselect CSH C18, 5 μm, 19×50 mm column using either a gradient of either 0.1% Formic Acid in MeCN in 0.1% aqueous Formic Acid or a gradient of MeCN in aqueous 10 mM Ammonium Bicarbonate; or a Waters Xbridge BEH C18, 5 μm, 19×50 mm column using a gradient MeCN in aqueous 10 mM Ammonium Bicarbonate. Fractions were collected following detection by UV at a single wavelength measured by a variable wavelength detector on a Gilson 215 preparative HPLC or Varian PrepStar preparative HPLC; by mass and UV at a single wavelength measured by a ZQ single quadrupole mass spectrometer, with positive and negative ion electrospray, and a dual wavelength detector on a Waters FractionLynx LCMS.

¹H NMR Spectroscopy: 1H NMR spectra were acquired on a Bruker Avance III spectrometer at 400 MHz. Either the central peaks of chloroform-d, dimethylsulfoxide-d6 or an internal standard of tetramethylsilane were used as references.

¹H NMR Spectroscopy:

¹H NMR spectra were acquired on a Bruker Avance III spectrometer at 400 MHz using residual undeuterated solvent as reference Example 1

4-(2-(6-(3,5-dimethylisoxazol-4-yl)-2-(1-(3-fluoro-4-methoxyphenyl)propan-2-yl)-3H-imidazo[4,5-b]pyridin-3-yl)ethyl)morpholine bis hydrochloride 5-bromo-N-(2-morpholinoethyl)-3-nitropyridin-2-amine

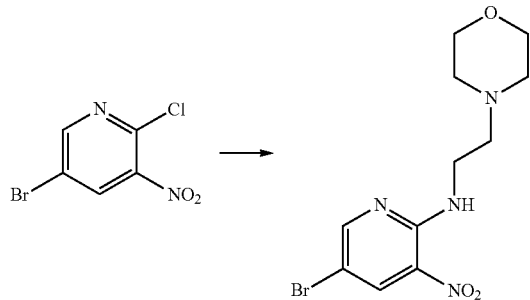 [SMILES: O=[N+]([O-])c1cc(Br)cnc1Cl ; O=[N+]([O-])c1cc(Br)cnc1NCCN1CCOCC1]

2-morpholinoethanamine (16.58 ml, 126 mmol) in THF (25 mL) was added to 5-bromo-2-chloro-3-nitropyridine (10 g, 42.1 mmol) in THF (50 mL) in a ice-water bath and the resulting mixture stirred at room temperature for 19 hours. The mixture was poured on ice-water (400 mL) and the yellow precipitate was filtered off, washed with water (100 mL) and dried in the vacuum oven to afford 5-bromo-N-(2-morpholinoethyl)-3-nitropyridin-2-amine (10.85 g, 76%) as a yellow product; m/z 331/333 (M+H)+ (ES+).

5-(3,5-dimethylisoxazol-4-yl)-N-(2-morpholinoethyl)-3-nitropyridin-2-amine

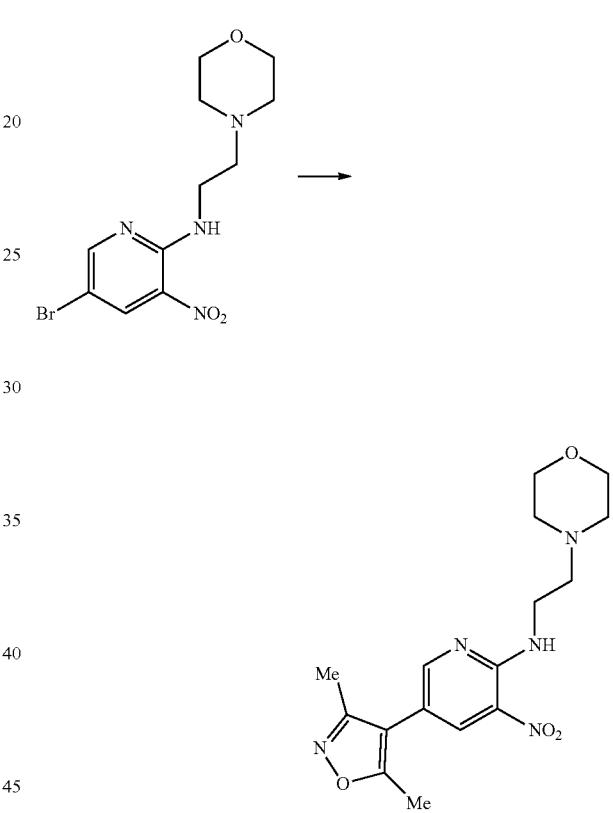

Tetrakis(triphenylphosphine)palladium(0) (1.745 g, 1.510 mmol) was added under nitrogen to a stirring slurry of sodium carbonate (4.80 g, 45.3 mmol), 5-bromo-N-(2-morpholinoethyl)-3-nitropyridin-2-amine (5 g, 15.10 mmol) and (3,5-dimethylisoxazol-4-yl)boronic acid (3.83 g, 27.2 mmol) in 1,4-dioxane/water (3:1, 100 mL), which had been previously sonicated and degassed with nitrogen. Following 10 further minutes under nitrogen with sonication, the thick mixture was stirred at 100° C. under nitrogen for 16 hours. The mixture was cooled down and extracted between brine (200 mL) and EtOAc (200 mL). The organic layer was further washed with brine (200 mL) and dried (Na₂SO₄). Flash chromatography (120 g, 0 to 100% ethyl acetate in isohexane) gave 5-(3,5-dimethylisoxazol-4-yl)-N-(2-morpholinoethyl)-3-nitropyridin-2-amine (4.55 g, 84%) as a bright orange oily solid; m/z 348 (M+H)+ (ES+).

5-(3,5-dimethylisoxazol-4-yl)-N²-(2-morpholino-ethyl)pyridine-2,3-diamine

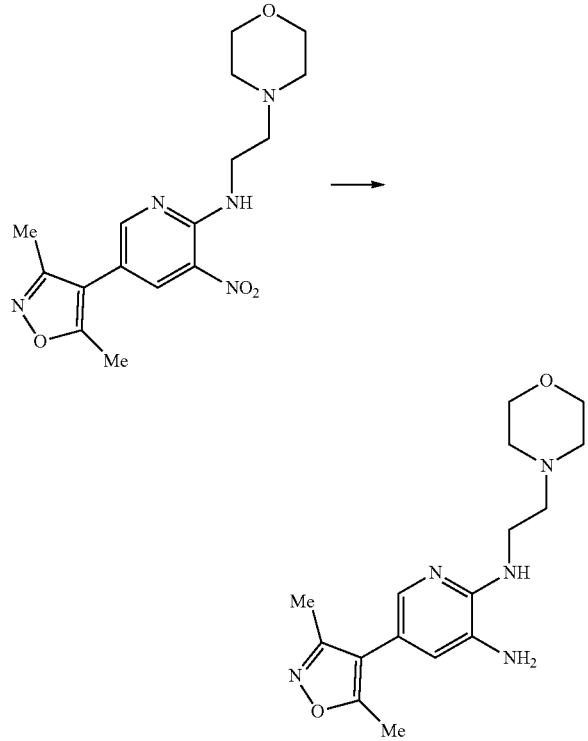

5% paladium on activated Carbon type 87L paste (500 mg) was added to 5-(3,5-dimethylisoxazol-4-yl)-N-(2-morpholinoethyl)-3-nitropyridin-2-amine in ethanol (100 mL). The mixture hydrogenated at a pressure of 5 bar overnight. LC-MS shows still 22% Starting material present so hydrogenated for further 4 hours. The mixture was filtered and evaporated in vacuo. The crude product was purified by chromatography on the Companion (120 g column, 0-10% MeOH in DCM to afford 5-(3,5-dimethylisoxazol-4-yl)-N2-(2-morpholinoethyl)pyridine-2,3-diamine (mg, %) as a dark green gum; m/z 318 (M+H)+ (ES+).

4-(2-(6-(3,5-dimethylisoxazol-4-yl)-2-(1-(3-fluoro-4-methoxyphenyl)propan-2-yl)-3H-imidazo[4,5-b]pyridin-3-yl)ethyl)morpholine bis hydrochloride

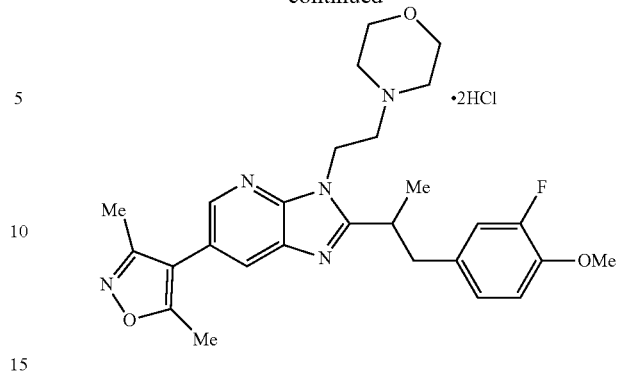

DIPEA (0.220 ml, 1.260 mmol) was added dropwise to a stirring solution of 5-(3,5-dimethylisoxazol-4-yl)-N²-(2-morpholinoethyl)pyridine-2,3-diamine (0.2 g, 0.630 mmol) 3-(3-fluoro-4-methoxyphenyl)-2-methylpropanoic acid (0.134 g, 0.630 mmol) and HATU (0.359 g, 0.945 mmol) in DMF (10 mL) and the resulting brown solution was stirred at room temperature for 16 hours. The mixture was treated with 2M NaOH (30 mL) and diluted with water and extracted with diethyl ether (2×150 mL). The organic layer was dried (MgSO4), filtered and evaporated under pressure to give intermediate as a brown oil. The oil was dissolved in acetic acid (2 mL) and heated to 100° C. overnight. The mixture was evaporated to dryness. The crude product was purified by chromatography on the Companion (40 g column, 0-100% ethyl acetate in isohexane. The free base was converted to the hydrochloride salt with 1M HCl in ethyl acetate to give 4-(2-(6-(3,5-dimethylisoxazol-4-yl)-2-(1-(3-fluoro-4-methoxyphenyl)propan-2-yl)-3H-imidazo[4,5-b]pyridin-3-yl)ethyl)morpholine bis-hydrochloride 1 (160 mg, 44%) as a cream solid; Rt 1.53 min; m/z 494 (M+H)+ (ES+); 1H NMR (d6-DMSO) δ: 11.82 (s, 1H), 8.37 (d, 1H), 8.15 (d, 1H), 7.23 (d, 1H), 7.10-7.00 (m, 2H), 4.79 (t, 2H), 4.09-3.92 (m, 2H), 3.91-3.80 (m, 2H), 3.78 (s, 3H), 3.77-3.71 (m, 1H), 3.69-3.59 (m, 1H), 3.59-3.45 (m, 1H), 3.41-3.29 (m, 1H), 3.27-3.13 (m, 3H), 3.17 (dd, 1H), 2.93 (dd, 1H), 2.42 (s, 3H), 2.24 (s, 3H), 1.32 (d, 3H).

Example 2

4-(2-(6-(3,5-dimethylisoxazol-4-yl)-2-(3-fluoro-4-methoxyphenethyl)-3H-imidazo[4,5-b]pyridin-3-yl)ethyl)morpholine)

5-bromo-N²-(2-morpholinoethyl)pyridine-2,3-diamine

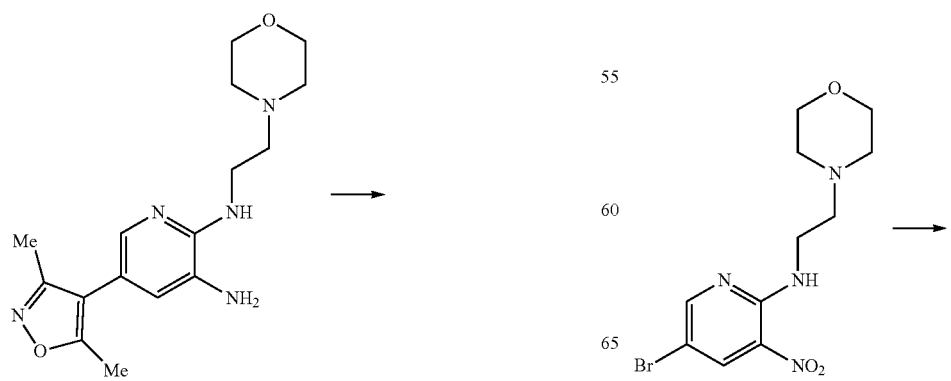

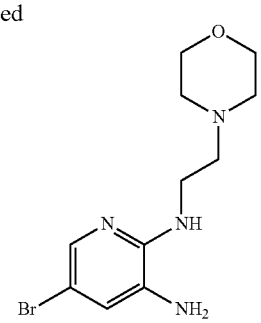

Concentrated aqueous ammonium hydroxide (1.5 ml, 38.5 mmol) followed by sodium dithionite (4.64 g, 22.65 mmol) were added to 5-bromo-N-(2-morpholinoethyl)-3-nitropyridin-2-amine (0.75 g, 2.265 mmol) in THF/water (120 mL). The mixture was stirred for 30 mn then extracted into EtOAc (100 mL). The organic layer was washed with brine (100 mL), dried (MgSO4) and evaporated in vacuo to give 5-bromo-N2-(2-morpholinoethyl)pyridine-2,3-diamine (500 mg, 1.577 mmol, 69.6% yield) as a pink oil; m/z 301/303 (M+H)+ (ES+).

4-(2-(6-bromo-2-(3-fluoro-4-methoxyphenethyl)-3H-imidazo[4,5-b]pyridin-3-yl)ethyl)morpholine

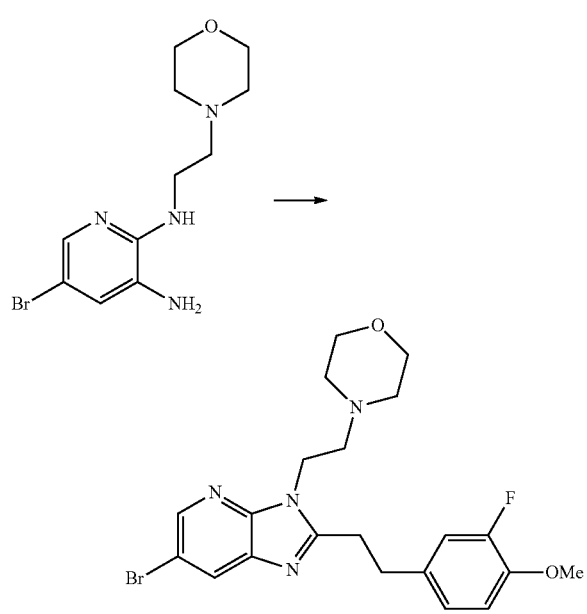

2,4,6-Tripropyl-1,3,5,2,4,6-trioxatriphosphinane 2,4,6-trioxide in EtOAc (4.89 ml, 8.30 mmol) was added to 5-bromo-N2-(2-morpholinoethyl)pyridine-2,3-diamine (0.5 g, 1.660 mmol), DIPEA (0.313 ml, 1.793 mmol) and 3-(3-fluoro-4-methoxyphenyl)propanoic acid (0.355 g, 1.793 mmol) in EtOAc (2 mL). The resulting mixture was stirred at 80° C. for 4.5 hours then at 100° C. overnight. The mixture was treated with NaHCO3 (25 mL), DCM (25 mL) and the layers separated through a Phase Separator cartridge. Acetic acid (20 mL) was added and the mixture stirred at 100° C. for 2.5 days. The mixture was evaporated in vacuo and treated with 2N sodium hydroxide (15 mL) and DCM (20 mL). The organic layer was retrieved through a Phase Separator cartridge, and evaporated in vacuo into a red oil. The crude product was purified by flash chromatography on silica gel (40 g column, 0-4% MeOH in DCM) to give 4-(2-(6-bromo-2-(3-fluoro-4-methoxyphenethyl)-3H-imidazo[4,5-b]pyridin-3-yl) ethyl)morpholine (479 mg, 59%) as a light brown oil: m/z 463/465 (M+H)+ (ES+).

4-(2-(6-(3,5-dimethylisoxazol-4-yl)-2-(3-fluoro-4-methoxyphenethyl)-3H-imidazo[4,5-b]pyridin-3-yl)ethyl)morpholine

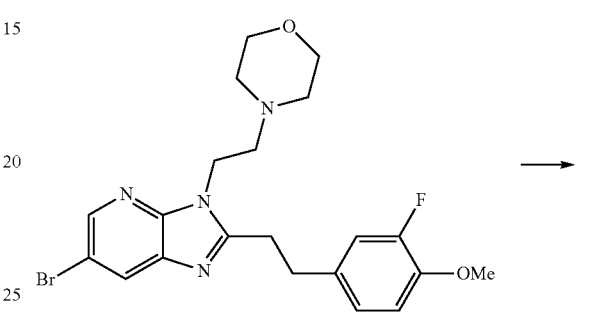

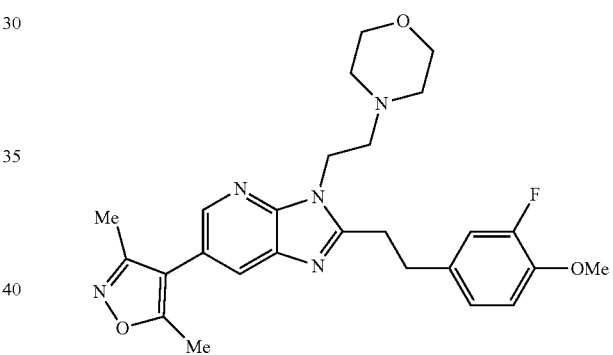

Tetrakis(triphenylphosphine)palladium(0) (37.4 mg, 0.032 mmol) was added under nitrogen to a stirring slurry of sodium (103 mg, 0.971 mmol), 4-(2-(6-bromo-2-(3-fluoro-4-methoxyphenethyl)-3H-imidazo[4,5-b]pyridin-3-yl)ethyl) morpholine (150 mg, 0.324 mmol) and (3,5-dimethylisoxazol-4-yl)boronic acid (82 mg, 0.583 mmol) in 3:1 1,4-dioxane/water (5 mL), which had been previously sonicated and degassed with nitrogen. Following 10 further minutes under nitrogen with sonication, the thick mixture was stirred at 100° C. under nitrogen for 3 hours. The mixture was cooled to room temperature, partitioned between DCM (15 mL) and brine (15 mL) and the organic layer retrieved through a Phase Separator and evaporated in vacuo. Flash chromatography (12 g, 0-3% MeOH in DCM) gave 4-(2-(6-(3,5-dimethylisoxazol-4-yl)-2-(3-fluoro-4-methoxyphenethyl)-3H-imidazo[4,5-b]pyridin-3-yl)ethyl) morpholine 2 (122 mg, 77%) as a light yellow oil; Rt 1.88 min (Method 1); m/z 480 (M+H)+ (ES+); 1H NMR (d6-DMSO) δ: : 8.28 (d, 1H), 8.04 (d, 1H), 7.27-7.19 (m, 1H), 7.12-7.05 (m, 2H), 4.36 (t, 2H), 3.81 (s, 3H), 3.49 (t, 4H), 3.31-3.25 (m, 2H), 3.21-3.13 (m, 2H), 2.64 (t, 2H), 2.45 (t, 4H), 2.43 (s, 3H), 2.25 (s, 3H).

Example 3

4-(2-(4-methoxyphenethyl)-3-(2-(tetrahydro-2H-pyran-4-yl)ethyl)-3H-imidazo[4,5-b]pyridin-6-yl)-3,5-dimethylisoxazole

5-bromo-3-nitro-N-(2-(tetrahydro-2H-pyran-4-yl)ethyl)pyridin-2-amine

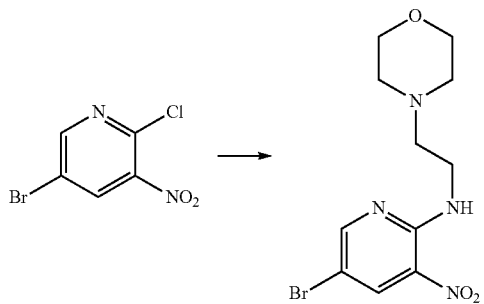 [SMILES: O=[N+]([O-])c1cc(Br)cnc1Cl ; O=[N+]([O-])c1cc(Br)cnc1NCCN1CCOCC1]

5-bromo-2-chloro-3-nitropyridine (5.73 g, 24.15 mmol) was dissolved in dry THF (50 ml, 610 mmol) and TEA (10.10 ml, 72.4 mmol) under nitrogen, 2-(tetrahydro-2H-pyran-4-yl)ethanamine hydrochloride (5 g, 30.2 mmol) was added and the resulting suspension stirred at RT over the weekend. The reaction mixture was poured onto ice/water (100 ml), the resulting yellow precipitate filtered off, washed with ice cold water (25 ml), dried in vacuo to give (7.49 g, 92%) as a bright yellow solid; m/z 330/332 (M+H)$^+$ (ES$^+$).

5-bromo-$N^2$-(2-(tetrahydro-2H-pyran-4-yl)ethyl)pyridine-2,3-diamine

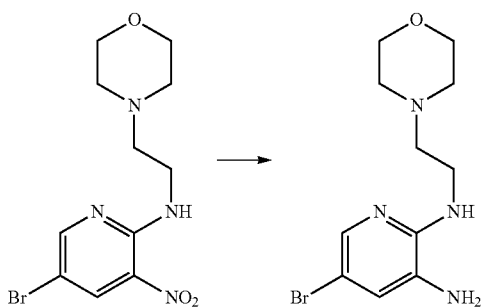 [SMILES: O=[N+]([O-])c1cc(Br)cnc1NCCN1CCOCC1 ; Nc1cc(Br)cnc1NCCN1CCOCC1]

5-bromo-3-nitro-N-(2-(tetrahydro-2H-pyran-4-yl)ethyl)pyridin-2-amine (3.5 g, 10.60 mmol) was dissolved in EtOH (150 ml, 2569 mmol), Pt-199 (type 29) (350 mg, 10.60 mmol) was added and the reaction mixture placed in the hydrogenation vessel. The reaction mixture was placed under H$_2$ (2 bar) overnight, with the vessel recharged twice to 2 bars. The reaction mixture was filtered through a bed of celite, rinse through with EtOH, the filtrates concentrated in vacuo to give (3.19 g, 95%) as a grey solid; m/z 300/302 (M+H)+ (ES+).

6-bromo-2-(4-methoxyphenethyl)-3-(2-(tetrahydro-2H-pyran-4-yl)ethyl)-3H-imidazo[4,5-b]pyridine

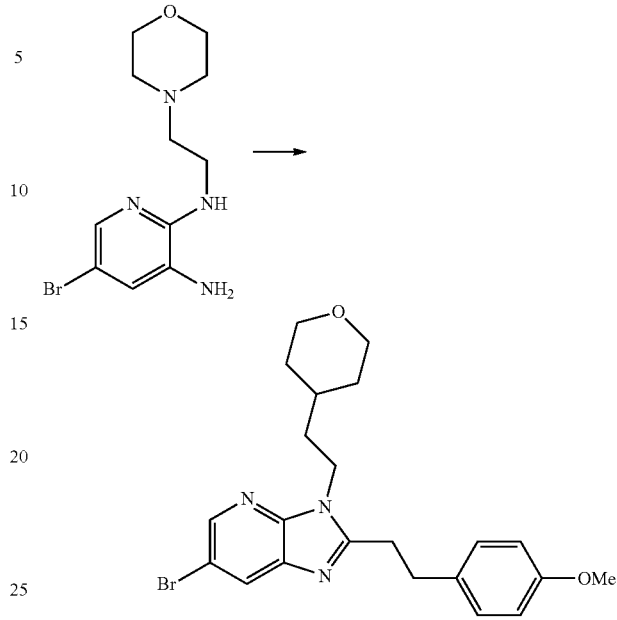

5-bromo-$N^2$-(2-(tetrahydro-2H-pyran-4-yl)ethyl)pyridine-2,3-diamine (2 g, 6.33 mmol), 3-(4-methoxyphenyl)propanoic acid (1.369 g, 7.60 mmol) and HATU (2.89 g, 7.60 mmol) were dissolved in dry DMF (40 ml, 517 mmol) under nitrogen. DIPEA (2.211 ml, 12.66 mmol) was added and the reaction mixture stirred at RT overnight. The reaction mixture was concentrated in vacuo, the residue dissolved in EtOAc (250 ml), washed with water (50 ml), saturated NaHCO$_3$ (50 ml), water (50 ml), brine (50 ml), the organics dried over MgSO4, filtered and concentrated in vacuo to give the amide intermediate, which was dissolved in glacial AcOH (45 ml, 786 mmol) and heated to 100° C. overnight, then at RT over the weekend. The reaction mixture was concentrated in vacuo, the residue taken up into EtOAc (200 ml), washed with NaHCO3 (50 ml), water (50 ml), brine (50 ml), dried over MgSO4, filtered and concentrated in vacuo to give a thick brown oil, which was purified by chromatography on the Companion (80 g Grace column, 0-10% MeCN in EtOAc, dry loaded) to give 6-bromo-2-(4-methoxyphenethyl)-3-(2-(tetrahydro-2H-pyran-4-yl)ethyl)-3H-imidazo[4,5-b]pyridine (2.05 g, 38%) as a red oil; m/z 444/446 (M+H)+ (ES+).

4-(2-(4-methoxyphenethyl)-3-(2-(tetrahydro-2H-pyran-4-yl)ethyl)-3H-imidazo[4,5-b]pyridin-6-yl)-3,5-dimethylisoxazole

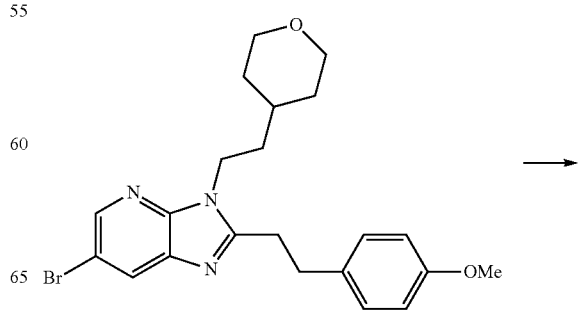

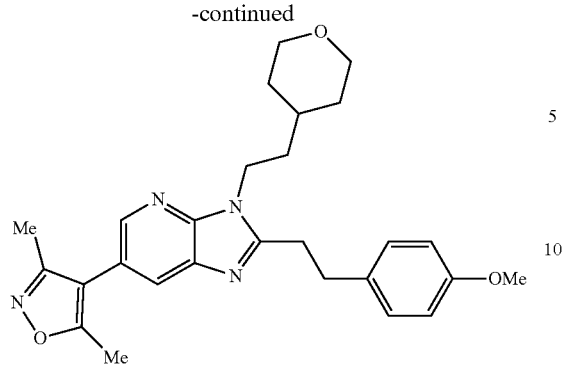

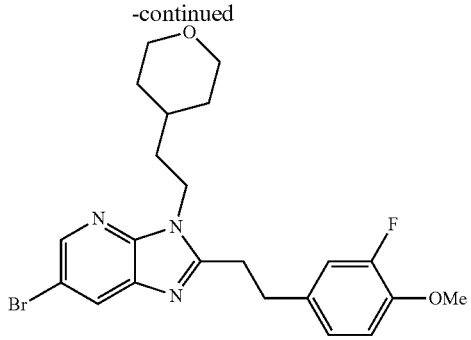

Tetrakis(triphenylphosphine)palladium(0) (65.0 mg, 0.056 mmol) was added to a slurry of sodium carbonate (179 mg, 1.688 mmol), 6-bromo-2-(4-methoxyphenethyl)-3-(2-(tetrahydro-2H-pyran-4-yl)ethyl)-3H-imidazo[4,5-b]pyridine (250 mg, 0.563 mmol) and (3,5-dimethylisoxazol-4-yl)boronic acid (119 mg, 0.844 mmol) in 3:1 1,4-dioxane/water (4 mL), which had been previously sonicated and degassed with nitrogen. The reaction mixture was stirred at 100° C. under nitrogen for 1 hour. After cooling to rt the reaction mixture was partitioned between ethyl acetate (30 ml) and water (10 ml). The organic phase was washed with brine (2×10 ml), collected and adsorbed onto silica. The crude material was purified by chromatography (4 g silica, 0-10% methanol in DCM, gradient elution) to afford 4-(2-(4-methoxyphenethyl)-3-(2-(tetrahydro-2H-pyran-4-yl)ethyl)-3H-imidazo[4,5-b]pyridin-6-yl)-3,5-dimethylisoxazole 3 (27 mg, 10%) as a sticky off white solid; Rt 2.06 min; m/z 461 (M+H)+ (ES+); 1H NMR (d6-DMSO) δ: 8.28 (d, 1H), 8.03 (d, 1H), 7.22 (d, 2H), 6.85 (d, 2H), 4.23 (t, 2H), 3.82 (dd, 2H), 3.71 (s, 3H), 3.28-3.22 (m, 2H), 3.22-3.17 (m, 2H), 3.16-3.10 (m, 2H), 2.42 (s, 3H), 2.24 (s, 3H), 1.65 (d, 2H), 1.62-1.55 (m, 2H), 1.55-1.46 (m, 1H), 1.20 (dd, 1H), 1.18 (dd, 1H).

Example 4

4-(2-(3-fluoro-4-methoxyphenethyl)-3-(2-(tetrahydro-2H-pyran-4-yl)ethyl)-3H-imidazo[4,5-b]pyridin-6-yl)-3,5-dimethylisoxazole 6-bromo-2-(3-fluoro-4-methoxyphenethyl)-3-(2-(tetrahydro-2H-pyran-4-yl)ethyl)-3H-imidazo[4,5-b]pyridine 5-bromo-N²-(2-(tetrahydro-2H-pyran-4-yl)ethyl)pyridine-2,3-diamine (0.6 g, 1.899 mmol), 3-(3-fluoro-4-methoxyphenyl)propanoic acid (0.452 g, 2.279 mmol) and HATU (0.866 g, 2.279 mmol) were dissolved in dry DMF (12 ml, 155 mmol) under nitrogen. DIPEA (0.663 ml, 3.80 mmol) was added and the reaction mixture stirred at RT overnight. The reaction mixture was concentrated in vacuo, the residue dissolved in EtOAc (125 ml), washed with water (25 ml), saturated NaHCO3 (25 ml), water (25 ml), brine (25 ml), the organics dried over MgSO4, filtered and concentrated in vacuo to give the amide intermediate, which was dissolved in glacial AcOH (25 ml, 437 mmol) and heated to 100° C. overnight, then at RT over the weekend. The reaction mixture was concentrated in vacuo, the residue taken up into EtOAc (100 ml), washed with NaHCO₃ (25 ml), water (25 ml), brine (25 ml), dried over MgSO4, filtered and concentrated in vacuo to give a brown oil, 990 mg. LCMS showed this to be ~95% product. The crude product was purified by chromatography on the Companion (40 g column, 0-5% MeCN in EtOAc, dry loaded) to give 6-bromo-2-(3-fluoro-4-methoxyphenethyl)-3-(2-(tetrahydro-2H-pyran-4-yl)ethyl)-3H-imidazo[4,5-b]pyridine (562 mg, 57%) as a pink oil; m/z 462/464 (M+H)+ (ES+).

4-(2-(3-fluoro-4-methoxyphenethyl)-3-(2-(tetrahydro-2H-pyran-4-yl)ethyl)-3H-imidazo[4,5-b]pyridin-6-yl)-3,5-dimethylisoxazole

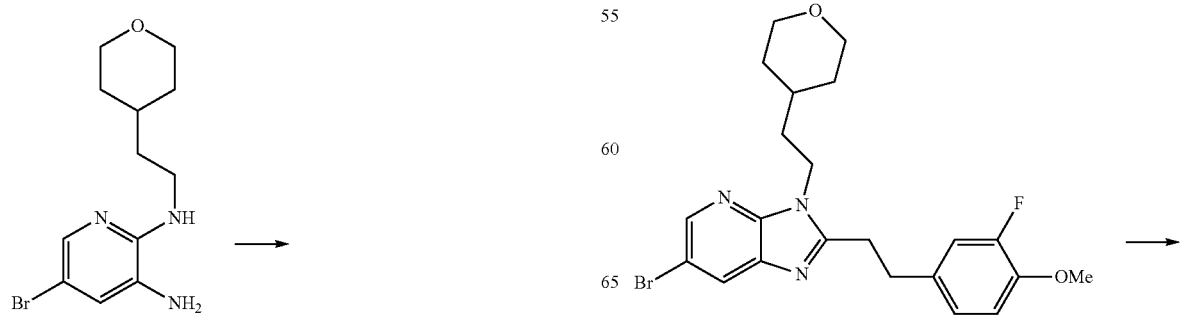

-continued

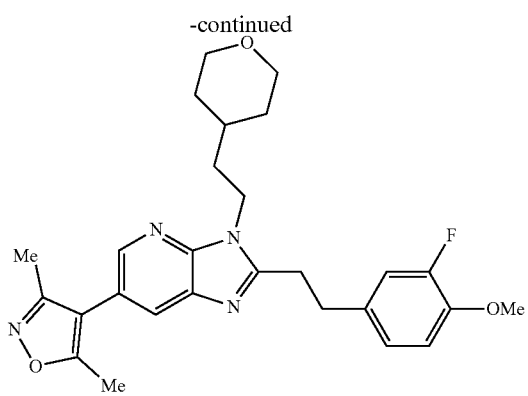

Tetrakis(triphenylphosphine)palladium(0) (62.5 mg, 0.054 mmol) was added under to a slurry of sodium carbonate (172 mg, 1.622 mmol), 6-bromo-2-(3-fluoro-4-methoxyphenethyl)-3-(2-(tetrahydro-2H-pyran-4-yl)ethyl)-3H-imidazo[4,5-b]pyridine (250 mg, 0.541 mmol) and (3,5-dimethylisoxazol-4-yl)boronic acid (114 mg, 0.811 mmol) in 1,4-dioxane/water (3:1, 4 mL), which had been previously sonicated and degassed with nitrogen. The reaction mixture was stirred at 100° C. under nitrogen for 1 hour. After cooling to rt the reaction mixture was partitioned between ethyl acetate (30 ml) and water (10 ml). The organic phase was washed with brine (2×10 ml), collected and adsorbed onto silica. The crude material was purified by chromatography (4 g silica, 0-10% methanol in DCM, gradient elution) followed by SCX chromatography to afford 4-(2-(3-fluoro-4-methoxyphenethyl)-3-(2-(tetrahydro-2H-pyran-4-yl)ethyl)-3H-imidazo[4,5-b]pyridin-6-yl)-3,5-dimethylisoxazole 4 (34 mg, 13%) as a gummy off white solid; Rt 2.11 min (Method 1); m/z 479 (M+H)+ (ES+); 1H NMR (d6-DMSO) δ: 8.28 (d, 1H), 8.04 (d, 1H), 7.21 (d, 1H), 7.10-7.03 (m, 2H), 4.25 (t, 2H), 3.84 (dd, 2H), 3.79 (s, 3H), 3.29-3.19 (m, 4H), 3.19-3.11 (m, 2H), 2.42 (s, 3H), 2.24 (s, 3H), 1.66 (d, 2H), 1.62-1.57 (m, 2H), 1.56-1.47 (m, 1H), 1.21 (dd, 1H), 1.17 (dd, 1H).

Example 5

4-(2-(6-(3,5-dimethylisoxazol-4-yl)-2-(3-fluoro-4-methoxyphenethyl)-3H-imidazo[4,5-b]pyridin-3-yl)ethyl)thiomorpholine-1,1-dioxide 4-(2-((5-bromo-3-nitropyridin-2-yl)amino)ethyl)thiomorpholine 1,1-dioxide

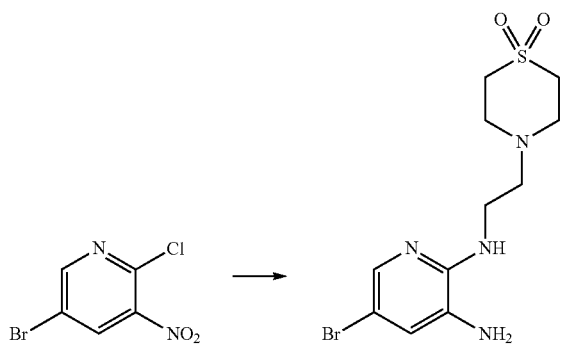 [SMILES: O=[N+]([O-])c1cc(Br)cnc1Cl ; Nc1cc(Br)cnc1NCCN1CCS(=O)(=O)CC1]

4-(2-aminoethyl)thiomorpholine 1,1-dioxide (1.051 g, 5.90 mmol) in THE (25 mL) was added dropwise to 5-bromo-2-chloro-3-nitropyridine (1.4 g, 5.90 mmol) and TEA (1.644 ml, 11.79 mmol) in THF (50 mL) in a ice-water bath and the resulting mixture stirred at room temperature for 19 hours. The mixture was poured on ice-water (400 mL) and the yellow precipitate was filtered off, washed with water (100 mL) and dried in the vacuum oven to afford product as a yellow solid. Acid/Base extraction removed the starting material to give 4-(2-((5-bromo-3-nitropyridin-2-yl)amino)ethyl)thiomorpholine 1,1-dioxide (1.01 g, 45%) as a crystalline yellow solid; m/z 379/381 (M+H)+ (ES+).

4-(2-((5-(3,5-dimethylisoxazol-4-yl)-3-nitropyridin-2-yl)amino)ethyl)thiomorpholine 1,1-dioxide

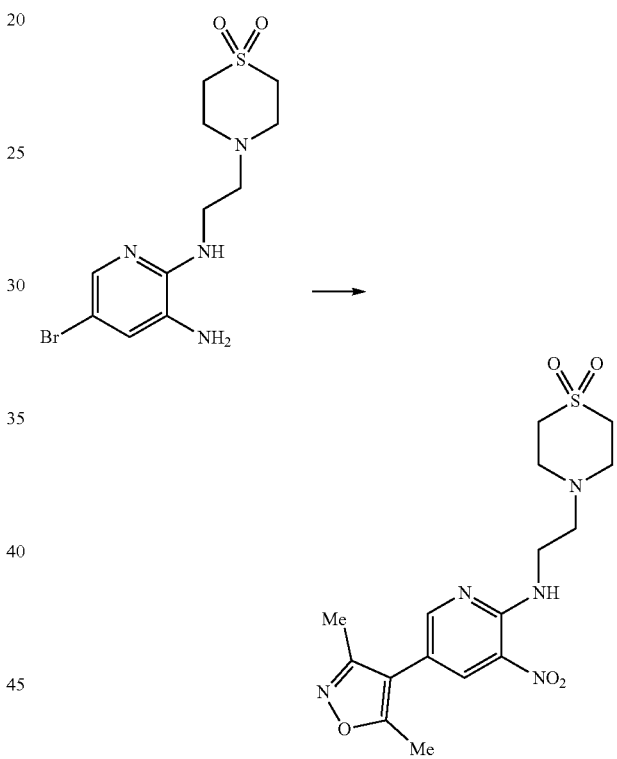

Tetrakis(triphenylphosphine)palladium(0) (0.308 g, 0.266 mmol) was added under nitrogen to a stirring slurry of sodium carbonate (0.847 g, 7.99 mmol), 4-(2-((5-bromo-3-nitropyridin-2-yl)amino)ethyl)thiomorpholine-1,1-dioxide (1.01 g, 2.66 mmol) and (3,5-dimethylisoxazol-4-yl)boronic acid (0.676 g, 4.79 mmol) in 1,4-dioxane/water (3:1, 40 mL), which had been previously sonicated and degassed with nitrogen. Following 10 further minutes under nitrogen with sonication, the thick mixture was stirred at 100° C. under nitrogen for 3 hours. The mixture was cooled down and acidified with 1M HCl, extracted with ethyl acetate (100 mL). The aqueous layer was re-basified with 2M NaOH and extracted with EtOAc (200 mL). The organic layer was further washed with brine (200 mL) and dried (MgSO₄) to give 4-(2-((5-(3,5-dimethylisoxazol-4-yl)-3-nitropyridin-2-yl)amino)ethyl)thiomorpholine 1,1-dioxide (1.03 g, 88%) as a brown sticky solid; m/z 396 (M+H)+ (ES+).

4-(2-((3-amino-5-(3,5-dimethylisoxazol-4-yl)pyridin-2-yl)amino)ethyl)thiomorpholine 1,1-dioxide

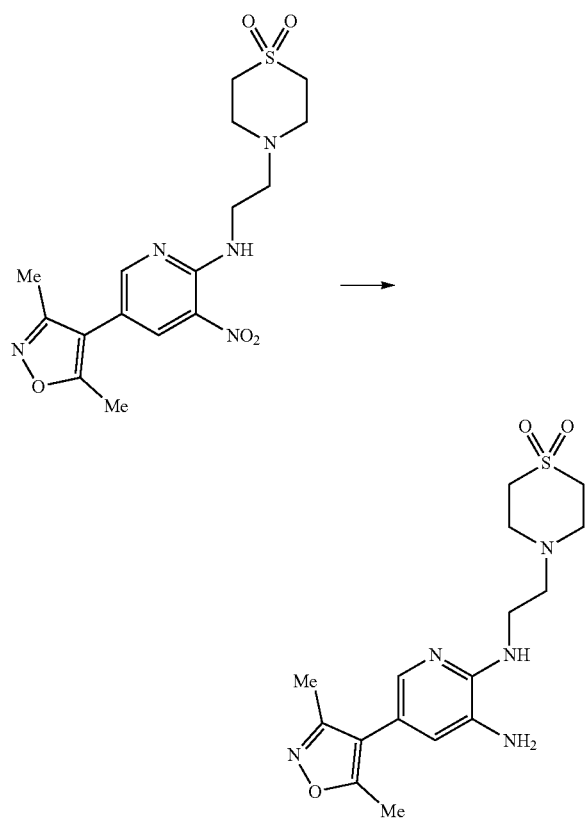

5% Paladium on activated Carbon type 87L paste (100 mg) was added to 4-(2-((5-(3,5-dimethylisoxazol-4-yl)-3-nitropyridin-2-yl)amino)ethyl)thiomorpholine 1,1-dioxide (1.03 g, 2.60 mmol) in ethanol (50 mL). The vessel was charged with $H_2$ at a pressure of 5 bars overnight then the mixture was filtered through Celite and evaporated in vacuo. The crude product was purified by chromatography on the Companion (40 g column, 0-10% MeOH in DCM) to give 4-(2-((3-amino-5-(3,5-dimethylisoxazol-4-yl)pyridin-2-yl)amino)ethyl)thio morpholine 1,1-dioxide (0.44 g, 42%) as a brown gum; m/z 366 (M+H)+ (ES+).

4-(2-(6-(3,5-dimethylisoxazol-4-yl)-2-(3-fluoro-4-methoxyphenethyl)-3H-imidazo[4,5-b]pyridin-3-yl)ethyl)thiomorpholine-1,1-dioxide

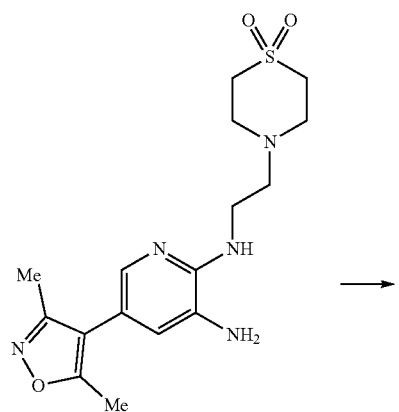

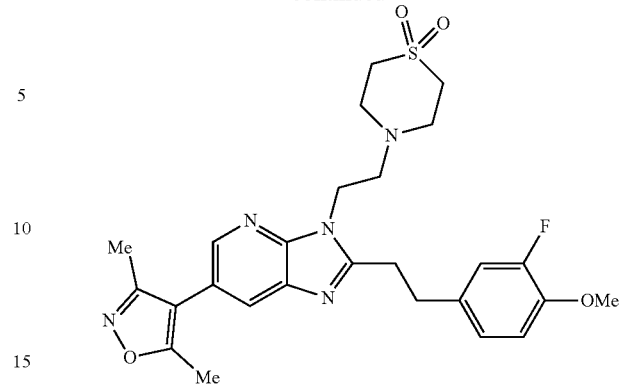

DIPEA (0.201 ml, 1.149 mmol) was added dropwise to a stirring solution of 4-(2-((3-amino-5-(3,5-dimethylisoxazol-4-yl)pyridin-2-yl)amino)ethyl)thiomorpholine 1,1-dioxide (0.21 g, 0.575 mmol) 3-(3-fluoro-4-methoxyphenyl)propanoic acid (0.114 g, 0.575 mmol) and HATU (0.328 g, 0.862 mmol) in DMF (10 mL) and the resulting brown solution was stirred at room temperature for 16 hours. The mixture was treated with 2M NaOH (30 mL) and diluted with water and extracted with diethyl ether (2×150 mL) (×2). The organic layer was dried (MgSO4), filtered and evaporated under pressure to give the amide intermediate, which was dissolved in acetic acid (2 mL) and heated to 100° C. overnight. The mixture was evaporated to dryness and the residue purified by flash chromatography on the Companion (40 g column, 0-10% MeOH in DCM) to afford the crude product. Further purification by flash chromatography (0-100% ethyl acetate in isohexanes) gave 4-(2-(6-(3,5-dimethylisoxazol-4-yl)-2-(3-fluoro-4-methoxyphenethyl)-3H-imidazo[4,5-b]pyridin-3-yl)ethyl)thiomorpholine 1,1-dioxide (114 mg, 36%) as an off-white solid; Rt 1.89 min (Method 1); m/z 528 (M+H)+(ES+); 1H NMR (d6-DMSO) δ: 8.27 (d, 1H), 8.04 (d, 1H), 7.27-7.20 (m, 1H), 7.12-7.04 (m, 2H), 4.36 (t, 2H), 3.80 (s, 3H), 3.31-3.24 (m, 2H), 3.19-3.12 (m, 2H), 2.98 (s, 8H), 2.86 (t, 2H), 2.42 (s, 3H), 2.24 (s, 3H).

Example 6

2-(6-(3,5-dimethylisoxazol-4-yl)-2-(3-fluoro-4-methoxyphenethyl)-3H-imidazo[4,5-b]pyridin-3-yl)-N-(tetrahydrofuran-3-yl)acetamide tert-butyl 2-((5-bromo-3-nitropyridin-2-yl)amino)acetate

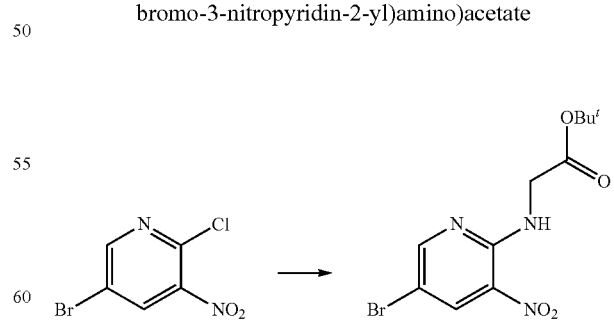

To a mixture of 5-bromo-2-chloro-3-nitropyridine (10 g, 42.1 mmol) and tert-butyl 2-aminoacetate hydrochloride (21.18 g, 126 mmol) in THF (50 mL) chilled in a water-bath was added TEA (29.4 ml, 211 mmol) in THF (15 mL) dropwise. The resulting orange mixture was stirred at room temperature for 24 hours then ice-water (250 mL) was added. The yellow precipitate was extracted into EtOAc (300 mL) and the organic layer washed with brine (300 mL), dried (MgSO4) and evaporated in vacuo to afford tert-butyl 2-((5-bromo-3-nitropyridin-2-yl)amino)acetate (11.85 g, 83%) as a brown oil; m/z 290/292 (M+H)+ (ES+).

tert-butyl 2-((5-(3,5-dimethylisoxazol-4-yl)-3-nitro-pyridin-2-yl)amino)acetate

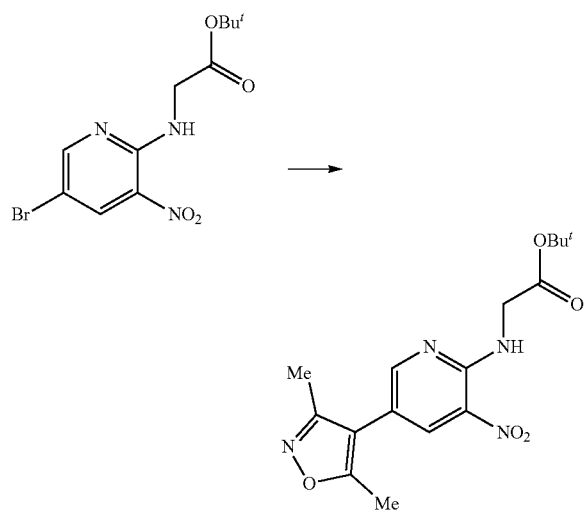

Tetrakis(triphenylphosphine)palladium(0) (2.73 g, 2.363 mmol) was added under nitrogen to a stirring slurry of sodium carbonate (7.51 g, 70.9 mmol), tert-butyl 2-((5-bromo-3-nitropyridin-2-yl)amino)acetate (7.85 g, 23.63 mmol) and (3,5-dimethylisoxazol-4-yl)boronic acid (6.00 g, 42.5 mmol) in 1,4-dioxane/water (3:1, 100 mL), which had been previously sonicated and degassed with nitrogen. Following 10 further minutes under nitrogen with sonication, the thick mixture was stirred at 100° C. under nitrogen for 16 hours. The mixture was cooled down and diluted with water (200 mL) and extracted with EtOAc (200 mL). The organic layer was further washed with brine (200 mL), dried (MgSO4), filtered off and evaporated in vacuo. The crude product was purified by chromatography on silica gel (220 g column, 0-100% DCM in isohexane) to afford tert-butyl 2-((5-(3,5-dimethylisoxazol-4-yl)-3-nitropyridin-2-yl) amino)acetate (4.28 g, 47%) as a orange solid; m/z 349 (M+H)+ (ES+).

tert-butyl 2-((3-amino-5-(3,5-dimethylisoxazol-4-yl) pyridin-2-yl)amino)acetate

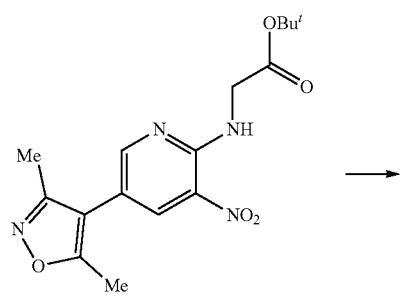

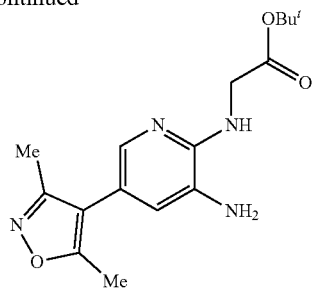

5% Palladium on activated Carbon type 87L paste (400 mg) was added to tert-butyl 2-((5-(3,5-dimethylisoxazol-4-yl)-3-nitropyridin-2-yl)amino)acetate (4.14 g, 11.88 mmol) in ethanol (50 mL). The vessel was charged with $H_2$ at a pressure of 1 bar over 44 h. The mixture was filtered and evaporated in vacuo to give tert-butyl 2-((3-amino-5-(3,5-dimethylisoxazol-4-yl)pyridin-2-yl)amino)acetate (3.32 g, 86%) as a dark brown oil; m/z 319 (M+H)+ (ES+).

2-(6-(3,5-Dimethylisoxazol-4-yl)-2-(3-fluoro-4-methoxyphenethyl)-3H-imidazo[4,5-b]pyridin-3-yl) acetic acid

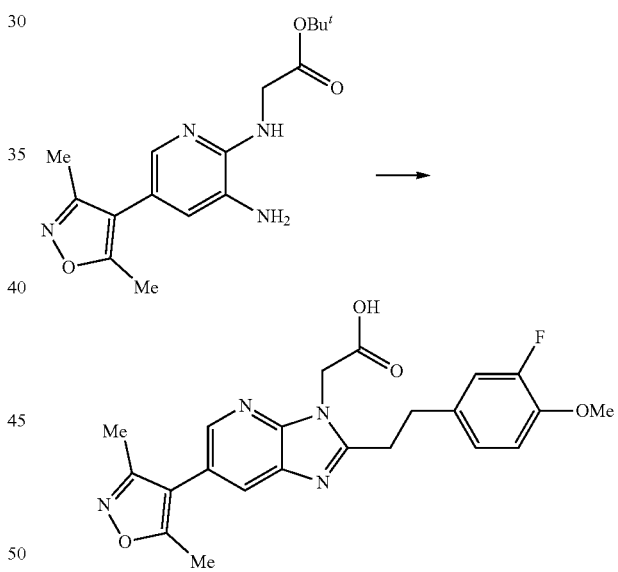

DIPEA (1.317 ml, 7.54 mmol) was added dropwise to a stirring solution of tert-butyl 2-((3-amino-5-(3,5-dimethyl-isoxazol-4-yl)pyridin-2-yl)amino)acetate (1.2 g, 3.77 mmol) 3-(3-fluoro-4-methoxyphenyl)propanoic acid (0.747 g, 3.77 mmol) and HATU (2.150 g, 5.65 mmol) in DMF (5 mL) and the resulting brown solution was stirred at room temperature for 16 hours. The mixture was treated with 2M NaOH (30 mL) and diluted with water and extracted with diethyl ether (2×150 mL) (X2). The organic layer was dried (MgSO4), filtered and evaporated under pressure to give intermediate as a brown oil. The oil was dissolved in acetic acid (5 mL) and heated to 100 C overnight. The mixture was evaporated to dryness and the residue was purified by chromatography on the Companion (40 g column, 0-10% MeOH in DCM to afford 2-(6-(3,5-dimethylisoxazol-4-yl)-2-(3-fluoro-4- methoxyphenethyl)-3H-imidazo[4,5-b]pyridin-3-yl)acetic acid (0.675 g, 21%) as a dark green solid; m/z 425 (M+H)+ (ES+).

2-(6-(3,5-dimethylisoxazol-4-yl)-2-(3-fluoro-4-methoxyphenethyl)-3H-imidazo[4,5-b]pyridin-3-yl)-N-(tetrahydrofuran-3-yl)acetamide 7 4-(2-(6-(3,5-dimethylisoxazol-4-yl)-2-(1-phenylpropan-2-yl)-3H-imidazo[4,5-b]pyridin-3-yl)ethyl)morpholine bis-hydrochloride

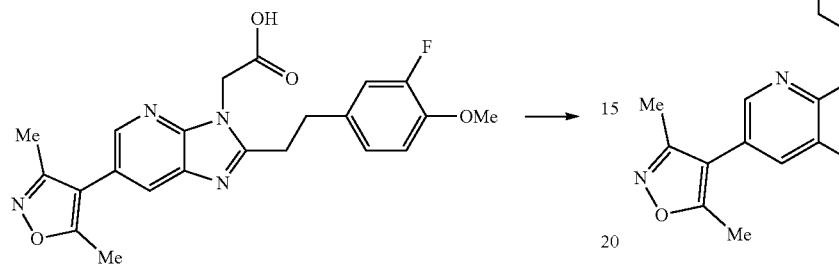

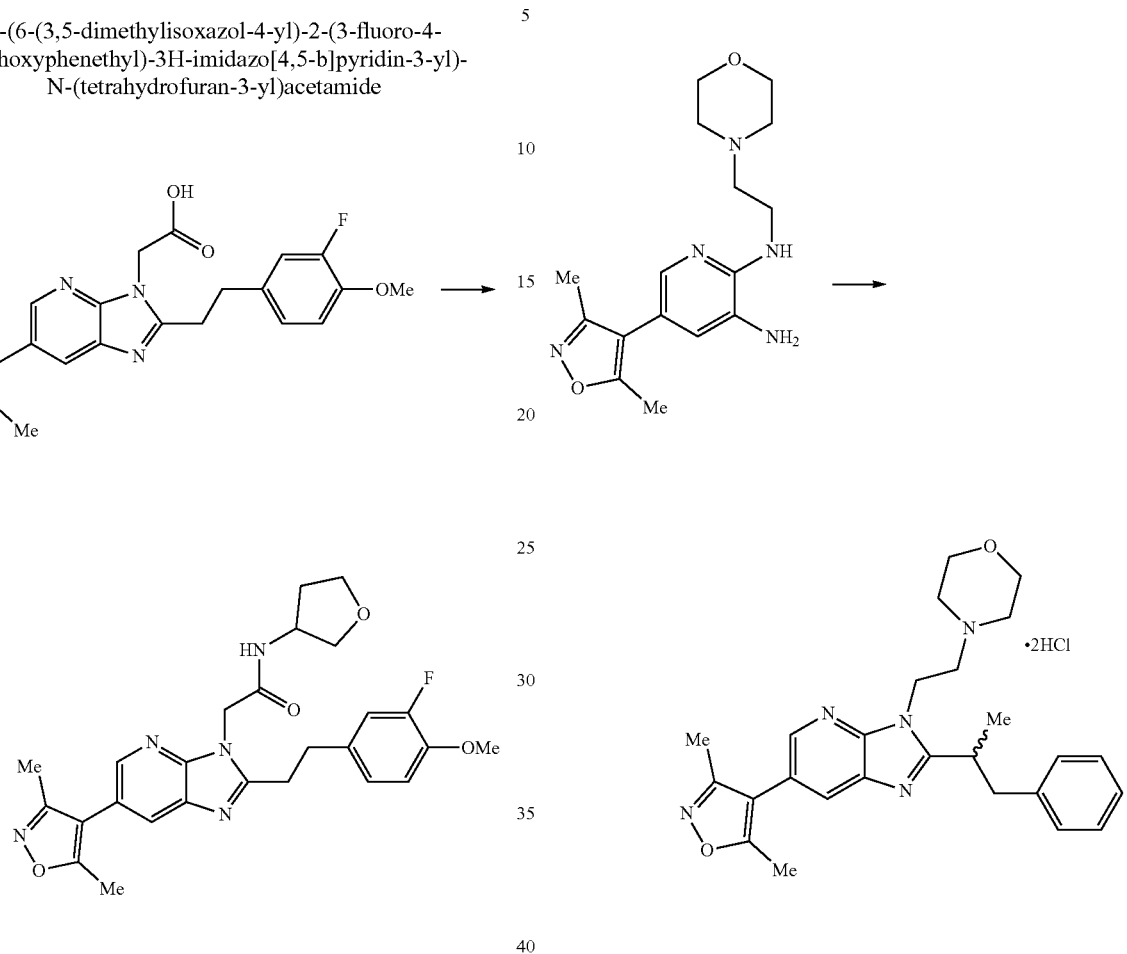

DIPEA (0.062 ml, 0.353 mmol) was added dropwise to a stirring solution of 2-(6-(3,5-dimethylisoxazol-4-yl)-2-(3-fluoro-4-methoxyphenethyl)-3H-imidazo[4,5-b]pyridin-3-yl)acetic acid (0.075 g, 0.177 mmol), tetrahydrofuran-3-amine (0.018 g, 0.212 mmol) and HATU (0.101 g, 0.265 mmol) in DMF (5 mL) and the resulting brown solution was stirred at room temperature for 16 hours. The mixture was evaporated under pressure and the residue was purified by preparative HPLC (Waters, Acidic (0.1% Formic acid), Acidic, Waters X-Select Prep-C18, 5 μm, 19×50 mm column, 20-50% MeCN in Water) to afford 2-(6-(3,5-dimethylisoxazol-4-yl)-2-(3-fluoro-4-methoxyphenethyl)-3H-imidazo[4,5-b]pyridin-3-yl)-N-(tetrahydrofuran-3-yl) acetamide 6 (25 mg, 28%) as a light pink solid; Acidic, Rt 1.74 min (Method 1); m/z 494 (M+H)+ (ES+); 1H NMR (d6-DMSO) δ: : 8.73 (d, 1H), 8.27 (d, 1H), 8.06 (d, 1H), 7.26-7.18 (m, 1H), 7.12-7.04 (m, 2H), 4.98 (s, 2H), 4.31-4.21 (m, 1H), 3.86-3.81 (m, 1H), 3.81 (s, 3H), 3.74 (dd, 1H), 3.71-3.65 (m, 1H), 3.51 (dd, 1H), 3.18-3.09 (m, 4H), 2.42 (s, 3H), 2.25 (s, 3H), 2.20-2.05 (m, 1H), 1.84-1.69 (m, 1H).

A mixture of 5-(3,5-dimethylisoxazol-4-yl)-N2-(2-morpholinoethyl)pyridine-2,3-diamine (200 mg, 0.630 mmol), 2-methyl-3-phenylpropanoic acid (103 mg, 0.630 mmol), T3P (50% wt in EtOAc) (938 μl, 3.15 mmol), DIPEA (121 μl, 0.693 mmol) in EtOAc (3151 μl, 0.630 mmol) was added at 70° C. overnight. The mixture was diluted with saturated aqueous NaHCO3 (10 mL), extracted with ethyl acetate (15 mL), dried (MgSO4) and evaporated to dryness. The oil was redissolved in glacial acetic acid (3 mL) and heated at 100° C. for 16 hours. The mixture was cooled to RT and the volatile was removed in vacuo. The crude product was purified by chromatography on the Companion (12 g column, 0-10% MeOH in DCM followed by 0-100% ethyl acetate in isohexane. 1M HCl in ethyl acetate was added to the crude product in ethyl acetate to afford 4-(2-(6-(3,5-dimethylisoxazol-4-yl)-2-(1-phenylpropan-2-yl)-3H-imidazo[4,5-b]pyridin-3-yl)ethyl)morpholine bis-hydrochloride (0.047 g, 14%) as a cream solid; Rt 1.32 min (Method 1); m/z 442 (M+H)+ (ES+); 1H NMR (d6-DMSO) δ: 11.63 (s, 1H), 8.35 (d, 1H), 8.16 (d, 1H), 7.32-7.24 (m, 4H), 7.23-7.17 (m, 1H), 4.71 (t, 2H), 4.55 (s, 2H), 4.04-3.93 (m, 2H), 3.90-3.78 (m, 2H), 3.57 (dd, 2H), 3.49-3.38 (m, 1H), 3.28-3.11 (m, 3H), 3.00 (dd, 1H), 2.43 (s, 3H), 2.25 (s, 3H), 1.36 (d, 3H).

Example 8

2-(6-(3,5-dimethylisoxazol-4-yl)-2-(3-fluoro-4-methoxyphenethyl)-3H-imidazo[4,5-b]pyridin-3-yl)-1-(4-hydroxypiperidin-1-yl)ethan-1-one 2-(6-(3,5-dimethylisoxazol-4-yl)-2-(3-fluoro-4-methoxyphenethyl)-3H-imidazo[4,5-b]pyridin-3-yl)-1-(4-hydroxypiperidin-1-yl)ethan-1-one

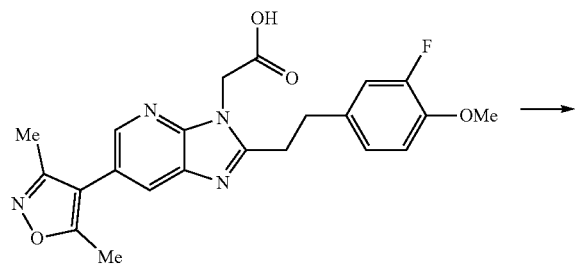

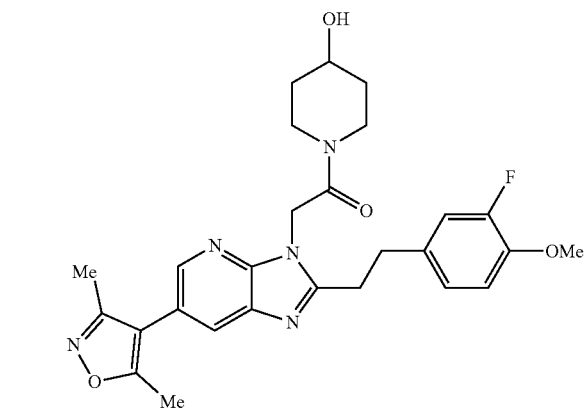

DIPEA (0.062 ml, 0.353 mmol) was added dropwise to a stirring solution of 2-(6-(3,5-dimethylisoxazol-4-yl)-2-(3-fluoro-4-methoxyphenethyl)-3H-imidazo[4,5-b]pyridin-3-yl) acetic acid (0.075 g, 0.177 mmol), piperidin-4-ol (0.021 g, 0.212 mmol) and HATU (0.101 g, 0.265 mmol) in DMF (5 mL) and the resulting brown solution was stirred at room temperature for 16 hours. The mixture was evaporated under pressure. The crude residue was purified by preparative HPLC (Waters, Acidic (0.1% Formic acid), Acidic, Waters X-Select Prep-C18, 5 μm, 19×50 mm column, 20-50% MeCN in Water) then by chromatography on silica gel (12 g column, 0-10% MeOH in DCM) to afford 2-(6-(3,5-dimethylisoxazol-4-yl)-2-(3-fluoro-4-methoxyphenethyl)-3H-imidazo[4,5-b]pyridin-3-yl)-1-(4-hydroxy piperidin-1-yl)ethanone (15 mg, 17%) as a light yellow solid; Rt 1.71 min (Method 1), m/z 508 (M+H)+ (ES+); 1H NMR (d6-DMSO) δ: : 8.25 (d, 1H), 8.06 (d, 1H), 7.21 (dd, 1H), 7.12-7.04 (m, 2H), 5.29 (d, 2H), 4.83 (d, 1H), 3.86 (dt, 2H), 3.81 (s, 3H), 3.79-3.71 (m, 1H), 3.40-3.31 (m, 2H), 3.12-3.05 (m, 4H), 2.42 (s, 3H), 2.25 (s, 3H), 1.93-1.82 (m, 1H), 1.77-1.66 (m, 1H), 1.56-1.44 (m, 1H), 1.35-1.23 (m, 1H).

Example 9

1-(4-((2-(1-(4-chlorophenyl)propan-2-yl)-5-(3,5-dimethylisoxazol-4-yl)-1H-benzo[d]imidazol-1-yl)methyl)piperidin-1-yl)ethan-1-one 1-(4-((2-(1-(4-chlorophenyl)propan-2-yl)-5-(3,5-dimethylisoxazol-4-yl)-1H-benzo[d]imidazol-1-yl)methyl)piperidin-1-yl)ethan-1-one

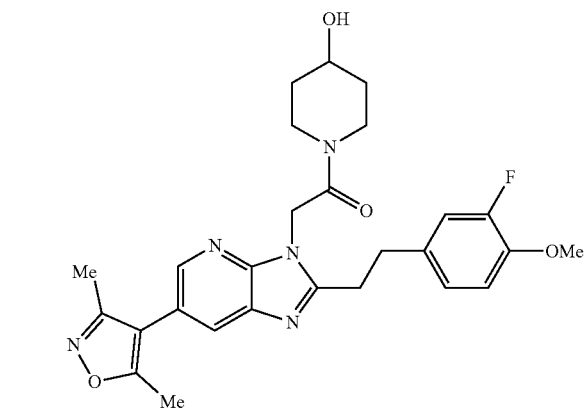

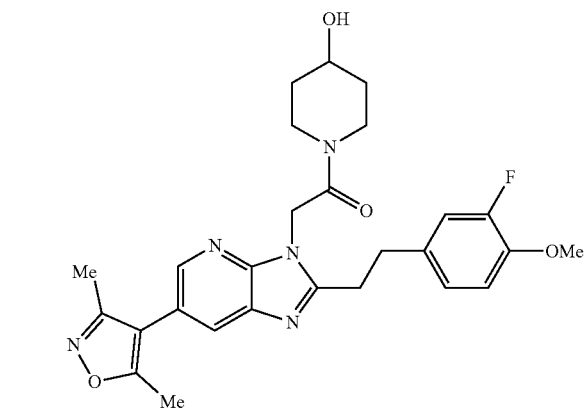

DIPEA (0.107 ml, 0.613 mmol) was added dropwise to a stirring solution of 2-(6-(3,5-dimethylisoxazol-4-yl)-2-(3-fluoro-4-methoxyphenethyl)-3H-imidazo[4,5-b]pyridin-3-yl)acetic acid (0.130 g, 0.306 mmol), oxetan-3-amine (0.022 g, 0.306 mmol) and HATU (0.175 g, 0.459 mmol) in DMF (5 mL) and the resulting brown solution was stirred at room temperature for 16 hours. The mixture was evaporated under pressure and the residue was purified by preparative HPLC (Waters, Acidic (0.1% Formic acid), Acidic, Waters X-Select Prep-C18, 5 μm, 19×50 mm column, 20-50% MeCN in Water) to afford 2-(6-(3,5-dimethylisoxazol-4-yl)-2-(3-fluoro-4-methoxyphenethyl)-3H-imidazo[4,5-b]pyridin-3-yl)-N-(oxetan-3-yl)acetamide (0.057 g, 37%) as a light grey solid; Rt 1.74 min (Method 1); m/z 480 (M+H)+ (ES+); 1H NMR (d6-DMSO) δ: 9.23 (d, 1H), 8.26 (d, 1H), 8.06 (d, 1H), 7.21 (dd, 1H), 7.12-7.03 (m, 2H), 5.01 (s, 2H), 4.87-4.77 (m, 1H), 4.73 (t, 2H), 4.46 (t, 2H), 3.81 (s, 3H), 3.19-3.06 (m, 4H), 2.42 (s, 3H), 2.24 (s, 3H).

Example 10

4-(2-(1-(3-fluoro-4-methoxyphenyl)propan-2-yl)-1-((tetrahydro-2H-pyran-4-yl)methyl)-1H-benzo[d]imidazol-5-yl)-3,5-dimethylisoxazole 4-(2-(1-(3-fluoro-4-methoxyphenyl)propan-2-yl)-1-((tetrahydro-2H-pyran-4-yl)methyl)-1H-benzo[d]imidazol-5-yl)-3,5-dimethylisoxazole

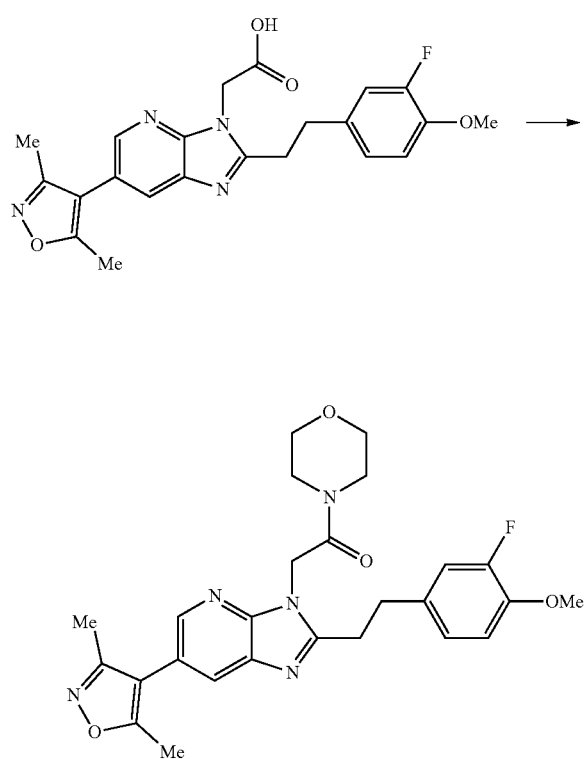

DIPEA (0.107 ml, 0.613 mmol) was added dropwise to a stirring solution of HATU (0.175 g, 0.459 mmol), morpholine (0.027 g, 0.306 mmol) and 2-(6-(3,5-dimethylisoxazol-4-yl)-2-(3-fluoro-4-methoxyphenethyl)-3H-imidazo[4,5-b]pyridin-3-yl)acetic acid (0.130 g, 0.306 mmol) in DMF (5 mL) and the resulting brown solution was stirred at room temperature for 16 hours. The mixture was evaporated under pressure and the residue was purified by preparative HPLC (Waters, Acidic (0.1% Formic acid), Acidic, Waters X-Select Prep-C18, 5 μm, 19×50 mm column, 35-65% MeCN in Water) to afford 2-(6-(3,5-dimethylisoxazol-4-yl)-2-(3-fluoro-4-methoxyphenethyl)-3H-imidazo[4,5-b]pyridin-3-yl)-1-morpholinoethanone (53 mg, 4.4%) as a light pink solid; Acidic, Rt 1.86 min (Method); m/z 494 (M+H)+ (ES+); 1H NMR (d6-DMSO) δ: 8.24 (d, 1H), 8.05 (d, 1H), 7.20 (dd, 1H), 7.12-7.04 (m, 2H), 5.30 (s, 2H), 3.80 (s, 3H), 3.75-3.68 (m, 2H), 3.68-3.63 (m, 2H), 3.63-3.55 (m, 2H), 3.50-3.41 (m, 2H), 3.15-3.05 (m, 4H), 2.42 (s, 3H), 2.24 (s, 3H).

Example 11

4-(2-(6-(3,5-dimethylisoxazol-4-yl)-2-(4-methoxyphenethyl)-3H-imidazo[4,5-b]pyridin-3-yl)ethyl)thiomorpholine 1,1-dioxide 4-(2-(6-(3,5-dimethylisoxazol-4-yl)-2-(4-methoxyphenethyl)-3H-imidazo[4,5-b]pyridin-3-yl)ethyl)thiomorpholine 1,1-dioxide DIPEA (0.201 ml, 1.149 mmol) was added dropwise to a stirring solution of 4-(2-((3-amino-5-(3,5-dimethylisoxazol-4-yl)pyridin-2-yl)amino)ethyl)thiomorpholine 1,1-dioxide (0.21 g, 0.575 mmol) 3-(4-methoxyphenyl)propanoic acid (0.104 g, 0.575 mmol) and HATU (0.328 g, 0.862 mmol) in DMF (10 mL) and the resulting brown solution was stirred at room temperature for 16 hours. The mixture was treated with 2M NaOH (30 mL) and diluted with water and extracted with diethyl ether (2×150 mL). The organic layer was dried (MgSO4), filtered and evaporated under pressure to give intermediate as a brown oil. The oil was dissolved in acetic acid (2 mL) and heated to 100° C. overnight. The mixture was evaporated to dryness and the residue was purified by chromatography on the Companion (40 g column, 0-10% MeOH in DCM), followed by further purification by flash chromatography to afford 4-(2-(6-(3,5-dimethylisoxazol-4-yl)-2-(4-methoxyphenethyl)-3H-imidazo[4,5-b]pyridin-3-yl)ethyl) thiomorpholine 1,1-dioxide (142 mg, 48%) as a off-white solid; Rt 1.83 min (Method 1); m/z 510 (M+H)+ (ES+); 1H NMR (d6-DMSO) δ: 8.27 (d, 1H), 8.04 (d, 1H), 7.24 (d, 2H), 6.86 (d, 2H), 4.33 (t, 2H), 3.72 (s, 3H), 3.30-3.21 (m, 2H), 3.19-3.11 (m, 2H), 2.97 (s, 8H), 2.84 (t, 2H), 2.42 (s, 3H), 2.24 (s, 3H).

Example 12

4-(2-(2-(2-(1H-indol-1-yl)ethyl)-6-(3,5-dimethyl-isoxazol-4-yl)-3H-imidazo[4,5-b]pyridin-3-yl)ethyl)morpholine bis-hydrochloride 4-(2-(2-(2-(1H-indol-1-yl)ethyl)-6-(3,5-dimethyl-isoxazol-4-yl)-3H-imidazo[4,5-b]pyridin-3-yl)ethyl)morpholine bis-hydrochloride

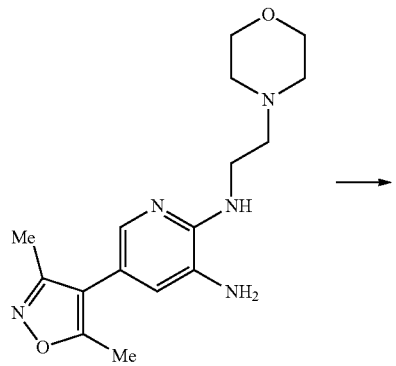

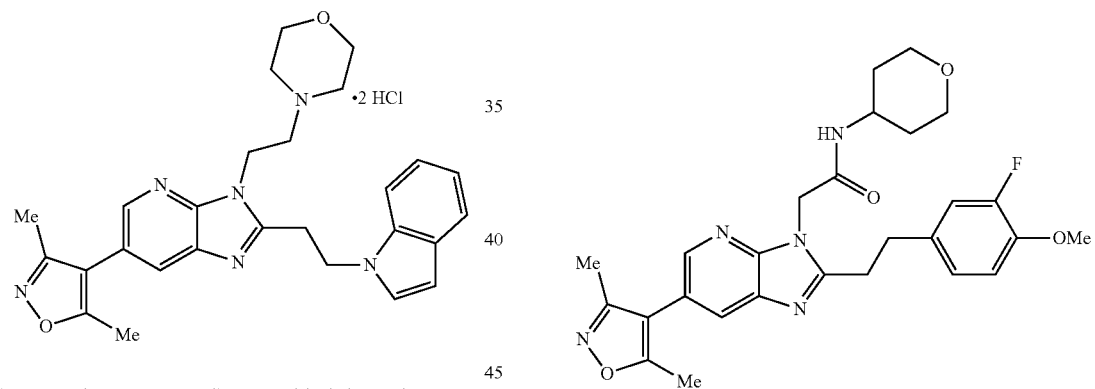

DIPEA (0.220 ml, 1.260 mmol) was added dropwise to a stirring solution of 5-(3,5-dimethylisoxazol-4-yl)-$N^2$-(2-morpholinoethyl)pyridine-2,3-diamine (0.2 g, 0.630 mmol) 3-(1H-indol-1-yl)propanoic acid (0.119 g, 0.630 mmol) and HATU (0.359 g, 0.945 mmol) in DMF (10 mL) and the resulting brown solution was stirred at room temperature for 16 hours. The mixture was treated with 2M NaOH (30 mL) and diluted with water and extracted with diethyl ether (2×150 mL). The organic layer was dried (MgSO$_4$), filtered and evaporated under pressure to give intermediate as a brown oil. The oil was dissolved in acetic acid (2 mL) and heated to 100° C. overnight. The mixture was evaporated to dryness and the residue was purified by chromatography on the Companion (40 g column, 0-10% MeOH in DCM). The crude product was converted to the HCl salt with 1M HCl in ethyl acetate to give 4-(2-(2-(2-(1H-indol-1-yl)ethyl)-6-(3,5-dimethylisoxazol-4-yl)-3H-imidazo[4,5-b]pyridin-3-yl)ethyl)morpholine bis-hydrochloride (142 mg, 41%) as a tan gum; The product was analysed by LCMS (Agilent, X-Select, Waters X-Select C18, 2.5 µm, 4.6×30 mm, Acidic (0.1% Formic acid) 4 min method, 5-95% MeCN/water): Rt 1.44 min (Method 1); m/z 471 (M+H)+ (ES+); 1H NMR (d6-DMSO) δ: 11.28 (s, 1H), 8.36 (d, 1H), 8.18 (d, 1H), 7.59-7.54 (m, 2H), 7.50 (d, 1H), 7.14 (ddd, 1H), 7.04 (ddd, 1H), 6.46 (dd, 1H), 4.81 (t, 2H), 4.65 (t, 2H), 3.97 (d, 2H), 3.75 (t, 2H), 3.59 (t, 2H), 3.52 (d, 2H), 3.43 (t, 2H), 3.10 (s, 2H), 2.44 (s, 3H), 2.26 (s, 3H).

Example 13

2-(6-(3,5-dimethylisoxazol-4-yl)-2-(3-fluoro-4-methoxyphenethyl)-3H-imidazo[4,5-b]pyridin-3-yl)-N-(tetrahydro-2H-pyran-4-yl)acetamide 2-(6-(3,5-dimethylisoxazol-4-yl)-2-(3-fluoro-4-methoxyphenethyl)-3H-imidazo[4,5-b]pyridin-3-yl)-N-(tetrahydro-2H-pyran-4-yl)acetamide

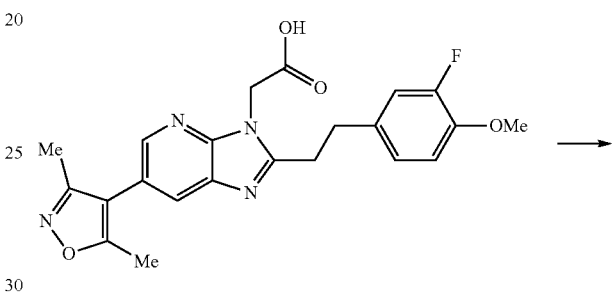

DIPEA (0.107 ml, 0.613 mmol) was added dropwise to a stirring solution of 2-(6-(3,5-dimethylisoxazol-4-yl)-2-(3-fluoro-4-methoxyphenethyl)-3H-imidazo[4,5-b]pyridin-3-yl)acetic acid (0.130 g, 0.306 mmol), tetrahydro-2H-pyran-4-amine (0.031 g, 0.306 mmol) and HATU (0.175 g, 0.459 mmol) in DMF (5 mL) and the resulting brown solution was stirred at room temperature for 16 hours. The mixture was evaporated under pressure and the residue was purified by preparative HPLC (Waters, Acidic (0.1% Formic acid), Acidic, Waters X-Select Prep-C18, 5 µm, 19×50 mm column, 20-50% MeCN in Water) to afford 2-(6-(3,5-dimethylisoxazol-4-yl)-2-(3-fluoro-4-methoxyphenethyl)-3H-imidazo[4,5-b]pyridin-3-yl)-N-(tetrahydro-2H-pyran-4-yl)acetamide (21 mg, 13%) as a light pink solid; Rt 1.78 min (Method 1); m/z 508 (M+H)+ (ES+); 1H NMR (d6-DMSO) δ: 8.49 (d, 1H), 8.28 (d, 1H), 8.07 (d, 1H), 7.24-7.17 (m, 1H), 7.12-7.04 (m, 2H), 4.99 (s, 2H), 3.86-3.81 (m, 2H), 3.81 (s, 3H), 3.80-3.73 (m, 1H), 3.34 (td, 2H), 3.20-3.07 (m, 4H), 2.42 (s, 3H), 2.25 (s, 3H), 1.72 (dd, 2H), 1.50-1.37 (m, 2H).

Example 14

(2S,6R)-4-(1-(6-(3,5-dimethylisoxazol-4-yl)-2-(4-methoxyphenethyl)-3H-imidazo[4,5-b]pyridin-3-yl)propan-2-yl)-2,6-dimethylmorpholine 1-((5-bromo-3-nitropyridin-2-yl)amino)propan-2-ol

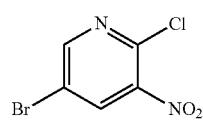  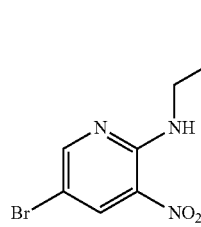

1-aminopropan-2-ol (3.25 ml, 42.1 mmol) in THF (10 mL) was added to 5-bromo-2-chloro-3-nitropyridine (5 g, 21.06 mmol) in THF (50 mL) cooled in ice-water (50 mL) to result in a yellow solution, then at room temperature for 16 hours. The orange solution was poured on ice-water (300 mL) and the precipitate stirred for 15 min and filtered off to give after drying 1-((5-bromo-3-nitropyridin-2-yl)amino)propan-2-ol (5.81 g, 100%) as a bright orange solid; m/z 277/279 (M+H)+ (ES+).

1-((3-Amino-5-bromopyridin-2-yl)amino)propan-2-ol

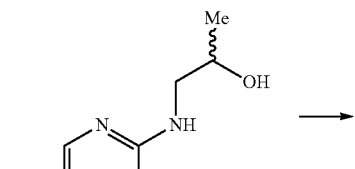  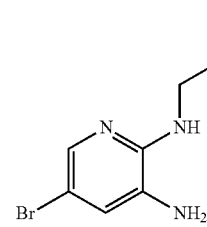

Concentrated aqueous ammonia (0.494 ml, 12.68 mmol) followed by sodium dithionite (26.0 g, 127 mmol) were added to 1-((5-bromo-3-nitropyridin-2-yl)amino)propan-2-ol (3.5 g, 12.68 mmol) in THF/water (12 mL). The mixture was stirred at RT for 16 hours before evaporating to dryness under vacuum. The solid was slurried in ethyl acetate (300 ml) for 30 minutes before filtering off. This was repeated once more to give 1-((3-amino-5-bromopyridin-2-yl)amino)propan-2-ol (1.68 g, 6.35 mmol, 50.1% yield) as a cream waxy solid; m/z 247/249 (M+H)+ (ES+).

1-(6-Bromo-2-(4-methoxyphenethyl)-3H-imidazo[4,5-b]pyridin-3-yl)propan-2-ol

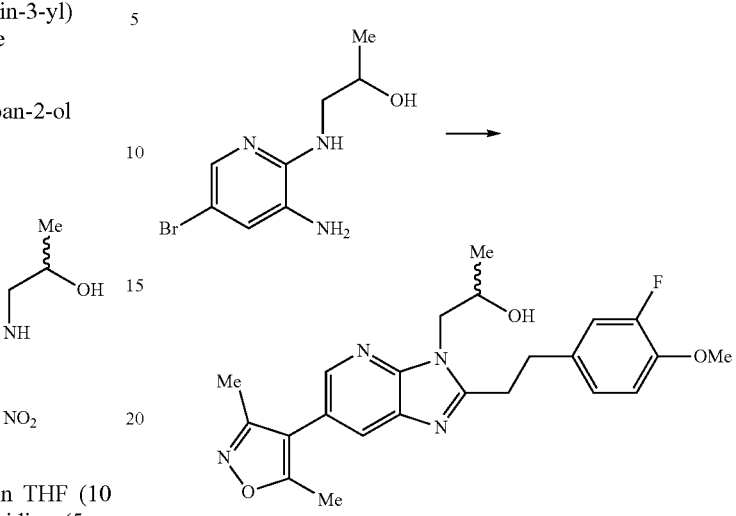

DIPEA (2.271 ml, 13.00 mmol) was added dropwise to a stirring solution of 1-((3-amino-5-bromopyridin-2-yl)amino)propan-2-ol (1.6 g, 6.50 mmol), 3-(4-methoxyphenyl)propanoic acid (1.757 g, 9.75 mmol) and HATU (3.71 g, 9.75 mmol) in DMF (25 mL) and the resulting brown solution was stirred at room temperature for 72 hours, then further 3-(4-methoxyphenyl) propanoic acid (1.757 g, 9.75 mmol), HATU (3.71 g, 9.75 mmol) and DIPEA (2.271 ml, 13.00 mmol) were added and stirring continued at RT overnight. The mixture was treated with 2M NaOH (30 mL) and diluted with water and extracted with diethyl ether (2×150 mL). The organic layer was dried (MgSO₄), filtered and evaporated under pressure to give the crude amide intermediate, which was redissolved in glacial acetic acid (20 ml, 5.51 mmol) and heated at 100° C. under nitrogen for 20 hours. The mixture was cooled and evaporated to dryness. The mixture was diluted with DCM (100 mL) and washed with saturated sodium bicarbonate solution (100 mL). The organic layer was separated, dried (MgSO4), filtered and evaporated to give the intermediate. The intermediate was dissolved in Methanol (30 mL) and treated with potassium carbonate (3.81 g, 27.6 mmol) before stirring at RT for 30 minutes. The mixture was evaporated to dryness and redissolved in ethyl acetate (100 mL), washed with water (100 mL), dried (MgSO₄), filtered and evaporated to dryness and triturated with diethyl ether to give 1-(6-bromo-2-(4-methoxyphenethyl)-3H-imidazo[4,5-b]pyridin-3-yl)propan-2-ol (1.635 g, 33%) as a light purple solid; m/z 390/392 (M+H)+ (ES+).

1-(6-(3,5-dimethylisoxazol-4-yl)-2-(4-methoxyphenethyl)-3H-imidazo[4,5-b]pyridin-3-yl)propan-2-ol

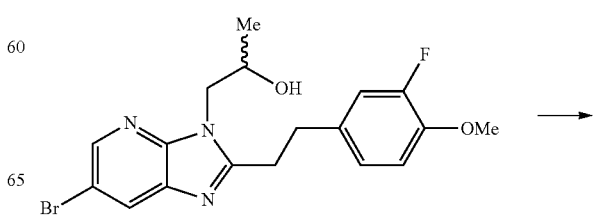

-continued

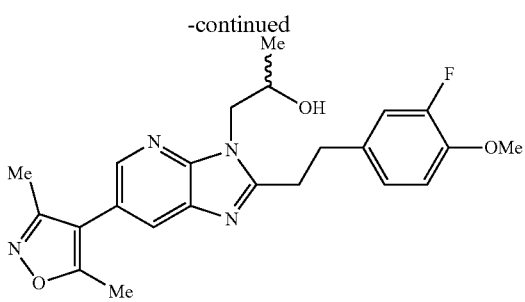

Tetrakis(triphenylphosphine)palladium(0) (0.484 g, 0.419 mmol) was added under nitrogen to a stirring slurry of sodium carbonate (1.332 g, 12.57 mmol), 1-(6-bromo-2-(4-methoxyphenethyl)-3H-imidazo[4,5-b]pyridin-3-yl)propan-2-ol (1.635 g, 4.19 mmol) and (3,5-dimethylisoxazol-4-yl) boronic acid (1.063 g, 7.54 mmol) in 1,4-dioxane/water (4:1, 40 mL), which had been previously sonicated and degassed with nitrogen. Following 10 further minutes under nitrogen with sonication, the thick mixture was stirred at 90° C. under nitrogen for 16 hours. The mixture was cooled down and extracted between brine (20 mL) and EtOAc (20 mL). The organic layer was further washed with brine (20 mL) and dried (Na2SO4) and evaporated in vacuo. The crude product was purified by chromatography on the Companion (80 g column, 0 to 100% ethyl acetate in isohexane to afford 1-(6-(3,5-dimethylisoxazol-4-yl)-2-(4-methoxyphenethyl)-3H-imidazo[4,5-b]pyridin-3-yl)propan-2-ol (1.32 g, 68%) as a cream solid; m/z 407.1 (M+H)+ (ES+).

1-(6-(3,5-dimethylisoxazol-4-yl)-2-(4-methoxyphenethyl)-3H-imidazo[4,5-b]pyridin-3-yl)propan-2-one

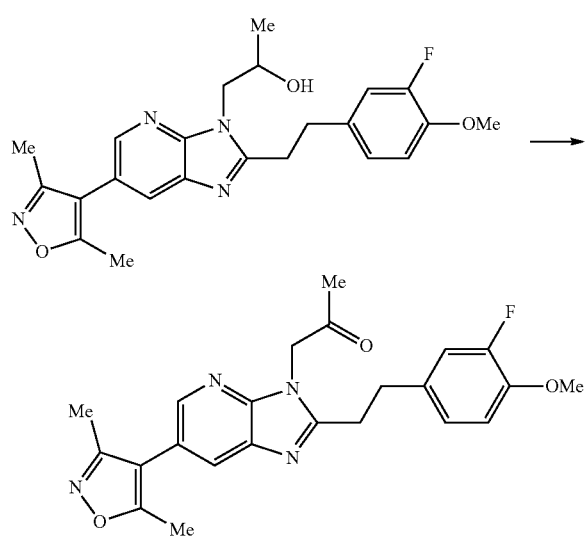

A mixture of 1-(6-(3,5-dimethylisoxazol-4-yl)-2-(4-methoxyphenethyl)-3H-imidazo[4,5-b]pyridin-3-yl)propan-2-ol (1.32 g, 3.25 mmol) and DMP (4.13 g, 9.74 mmol) in DCM (40 ml, 8.00 mmol) was stirred at room temperature for 72 hours. Further DMP (0.5 molar equivalent) was added and the mixture stirred for 16 hours. 2 M aqueous NaHCO3 was added until effervescence stopped. The layers were separated and the aqueous was extracted with DCM (3×100 mL). The combined organic layers were washed with brine (100 mL), dried (MgSO4), filtered and reduced in vacuo to give a yellow solid, which was purified by chromatography on the Companion (80 g column, 0-100% ethyl acetate in isohexane) to afford 1-(6-(3,5-dimethylisoxazol-4-yl)-2-(4-methoxyphenethyl)-3H-imidazo[4,5-b]pyridin-3-yl)propan-2-one (1.3 g, 79%) as a white solid; m/z 405 (M+H)+ (ES+).

(2S,6R)-4-(1-(6-(3,5-dimethylisoxazol-4-yl)-2-(4-methoxyphenethyl)-3H-imidazo[4,5-b]pyridin-3-yl) propan-2-yl)-2,6-dimethylmorpholine

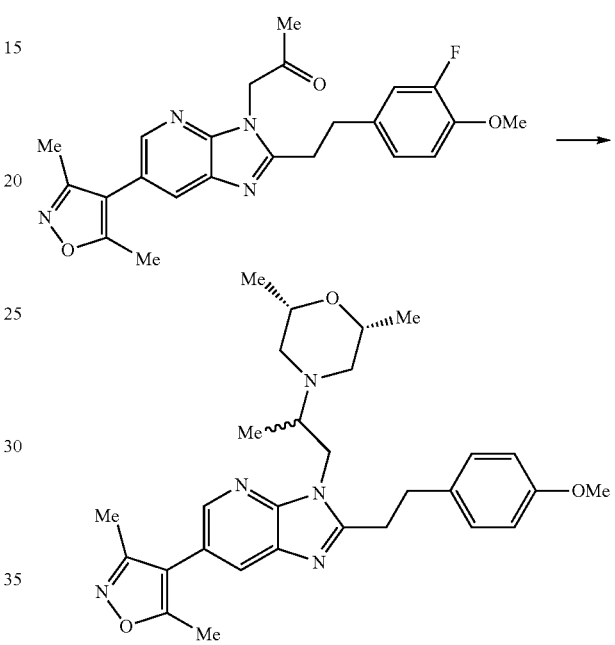

A solution of 1-(6-(3,5-dimethylisoxazol-4-yl)-2-(4-methoxyphenethyl)-3H-imidazo[4,5-b]pyridin-3-yl)propan-2-one (150 mg, 0.371 mmol), (2S,6R)-2,6-dimethylmorpholine (128 mg, 1.113 mmol) and titanium isopropoxide (329 μl, 1.113 mmol) in 1,2-dichloroethane (5 ml) was heated to 80° C. for 16 h. The mixture was treated with titanium isopropoxide (329 μl, 1.113 mmol) and heated for a further 4 h. After cooling to RT, sodium triacetoxyhydroborate (236 mg, 1.113 mmol) was added and the reaction mixture stirred at RT for 16 h. Saturated aqueous NaHCO$_3$ (10 ml) was added and the mixture stirred for 10 mins before collecting the organic phase via a PhaseSep cartridge. Silica was added and the solvents were removed in vacuo. The crude material was purified by chromatography (12 g silica, 0-10% methanol in DCM, gradient elution) then by preparative HPLC (Varian, Acidic (0.1% Formic acid), Acidic, Waters X-Select Prep-C18, 5 μm, 19×50 mm column, 15-35% MeCN in Water). The isolated fractions were evaporated in vacuo and the solid dissolved in 1M HCl in ethyl acetate to afford (2R,6S)-4-(1-(6-(3,5-dimethylisoxazol-4-yl)-2-(4-methoxyphenethyl)-3H-imidazo[4,5-b]pyridin-3-yl)propan-2-yl)-2,6-dimethylmorpholine bis-hydrochloride (28 mg, 12%) as a light brown solid; Rt 1.73 min (Method 1); m/z 504 (M+H)+ (ES+); 1H NMR (d6-DMSO) δ: 8.29 (d, 1H), 8.02 (d, 1H), 7.28 (d, 2H), 6.87 (d, 2H), 4.80 (dd, 1H), 4.54 (dd, 1H), 4.03 (s, 2H), 3.83-3.76 (m, 1H), 3.75 (s, 3H), 3.37-3.28 (m, 3H), 3.24-3.16 (m, 3H), 2.75 (t, 1H), 2.71-2.62 (m, 1H), 2.42 (s, 3H), 2.24 (s, 3H), 1.19 (d, 3H), 1.18 (d, 3H), 1.16 (d, 3H).

Example 15

2-(6-(3,5-dimethylisoxazol-4-yl)-2-(3-fluoro-4-methoxyphenethyl)-3H-imidazo[4,5-b]pyridin-3-yl)-1-(3-hydroxypyrrolidin-1-yl)ethan-1-one 2-(6-(3,5-dimethylisoxazol-4-yl)-2-(3-fluoro-4-methoxyphenethyl)-3H-imidazo[4,5-b]pyridin-3-yl)-1-(3-hydroxypyrrolidin-1-yl)ethan-1-one

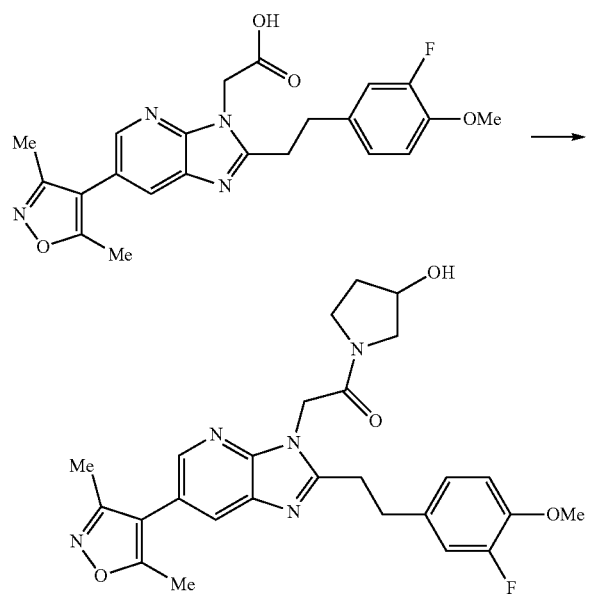

DIPEA (0.107 ml, 0.613 mmol) was added dropwise to a stirring solution of 2-(6-(3,5-dimethylisoxazol-4-yl)-2-(3-fluoro-4-methoxyphenethyl)-3H-imidazo[4,5-b]pyridin-3-yl)acetic acid (0.130 g, 0.306 mmol), pyrrolidin-3-ol (0.027 g, 0.306 mmol) and HATU (0.175 g, 0.459 mmol) in DMF (5 mL) and the resulting brown solution was stirred at room temperature for 16 hours. The mixture was evaporated under pressure and the residue was purified by preparative HPLC (Waters, Acidic (0.1% Formic acid), Acidic, Waters X-Select Prep-C18, 5 μm, 19×50 mm column, 20-50% MeCN in Water) to afford 2-(6-(3,5-dimethylisoxazol-4-yl)-2-(3-fluoro-4-methoxyphenethyl)-3H-imidazo[4,5-b]pyridin-3-yl)-1-(3-hydroxypyrrolidin-1-yl)ethanone (45 mg, 28%) as a light blue solid; Rt 1.64 min (Method 1); m/z 494 (M+H)+ (ES+); 1H NMR (d6-DMSO) δ: 8.24 (dd, 1H), 8.06 (d, 1H), 7.21 (d, 1H), 7.11-7.05 (m, 2H), 5.77 (s, 1H), 5.26-5.01 (m, 3H), 4.44 (s, 0.5H), 4.30 (s, 0.5H), 3.81 (s, 3H), 3.79-3.69 (m, 2H), 3.55-3.42 (m, 1H), 3.12 (s, 4H), 2.42 (s, 3H), 2.25 (s, 3H), 2.09-1.75 (m, 2H).

Example 16

Biological Testing

Surface Plasmon Resonance (BIAcore) Analysis of Binding to EP300 and BRD4 BD1

BIAcore data for compound binding to EP300 and BRD4 was acquired using a T200 BIAcore instrument at 4° C. His-tagged EP300 Bromodomain (1046-1163) and BRD4 Bromodomain 1 (49-170) proteins were captured onto an NTA chip via a combined capture and amine coupling method. NTA groups were first chelated with 30 mM nickel chloride and then activated with 0.2 M N-ethyl-N'-(diethylaminopropyl)-carbodiimide (EDC) and 0.05 M N-hydroxysuccimide (NHS).

Bromodomain proteins diluted to 9.6 μM in PBS 0.05% Tween-20 were injected at 10 μl/min and covalently bound. Ethanolamine injections were performed to cap unreacted moieties on the surface and remove uncoupled protein. A typical immobilisation resulted in ~2-4 kRU of protein immobilised on the surface. Test compounds were serially diluted to generate 1, 10, 100, 1000 and 10000 nM solutions in running buffer (PBS with 0.005% Tween-20, 0.1% DMSO). Using a flow rate of 90 μL/min throughout, runs consisted of injections of compound with escalating concentration, interspersed with buffer blank runs consisting of 5 repeat injections of running buffer.

Sensorgrams were analyzed with BIAevaluation (GE Healthcare) using a 1:1 interaction model to generate $k_a$ and $k_d$ values to describe the kinetics of binding. $K_D$ values were derived from the quotient of $k_d$ and $k_a$. All compounds were tested twice against the EP300 and BRD4 bromodomain surfaces to obtain geometric means of the kinetic and affinity parameters. All compounds tested gave $K_D$ values in the range of 0.5-10,000 nM.

Cell Viability Assay

The 22Rv1 cell line was obtained from ATCC (UK) and cultured according to the supplier's recommendations. Cell growth inhibitory activity of representative compounds was determined using the CellTiter-Glo® Luminescent Cell Viability Assay kit (Promega, USA).

22Rv1 cells were maintained in RPMI 1640 media containing 10% Foetal Bovine Serum, 2 mM Glutamine, 1 mM sodium pyruvate and 100 units of Penicillin-100 g of Streptomycin. Cells were incubated at 37° C. in a humidified atmosphere with 95% 02 and 5% $CO_2$. 2000 cells were seeded per well in Poly-D-Lysine (PDL) coated 96-well black clear bottom plates (VWR, UK) in 50 L of growth medium. After 48 hours, medium was removed and replaced with growth medium containing diluted test compounds. Compound dilutions were performed by serially diluting in half log intervals DMSO stocks at a maximum concentration of 10 mM, for a total of 7 dilutions. A 1 μl aliquot of each dilution point was added to 99 μl of growth medium and 50 μL added to each well containing cells, providing 100 μM compound at the maximum concentration point (1% DMSO). 1% DMSO treated cells served as a high control.

Cells were incubated for a further 72 hours at 37° C. and cell viability determined using the CellTiter-Glo® Luminescent Cell Viability Assay according to the manufacturer's instructions. Briefly, a volume of CellTiter-Glo® reagent equal to the volume of growth media was added to each well. Plates were shaken for approximately 2 minutes and incubated at room temperature (22° C.) for 10 minutes. The luminescence signal was measured using an Envision plate reader with an integration time of 1 second per well.

All data was normalised to the mean of 6 high-controls. The half maximum inhibitor concentration (IC50) was calculated from a 4-parameter logistic curve fit of the data using the Dotmatics software (UK). All compounds tested gave IC50 values in the range of 100 nM -100 μM, typically from 100 nM -30 μM.

Cell based assays are likely to show some variability due to the complexity of the system and it is understood that the results of these assays may vary as assay conditions are varied. Some level of cell growth inhibition is indicative of the compound having some inhibitory activity in specified cells, whereas lack of the inhibition below the highest concentration tested does not necessarily indicate the compound has no inhibitory activity on the cells.

Example 17

Tablet Composition

Tablets, each weighing 0.15 g and containing 25 mg of a compound of the invention are manufactured as follows:
Composition for 10,000 Tablets
Compound of the invention (250 g)
Lactose (800 g)
Corn starch (415 g)
Talc powder (30 g)
Magnesium stearate (5 g)

The compound of the invention, lactose and half of the corn starch are mixed. The mixture is then forced through a sieve 0.5 mm mesh size. Corn starch (10 g) is suspended in warm water (90 ml). The resulting paste is used to granulate the powder. The granulate is dried and broken up into small fragments on a sieve of 1.4 mm mesh size. The remaining quantity of starch, talc and magnesium is added, carefully mixed and processed into tablets.

Example 18

Injectable Formulation

| Compound of the invention | 200 mg |
| Hydrochloric Acid Solution 0.1M or Sodium Hydroxide Solution 0.1M q.s. | to pH 4.0 to 7.0 |
| Steriile water q.s. to | 10 mL |

The compound of the invention is dissolved in most of the water (35°-40° C.) and the pH adjusted to between 4.0 and 7.0 with the hydrochloric acid or the sodium hydroxide as appropriate. The batch is then made up to volume with water and filtered through a sterile micropore filter into a sterile 10 mL amber glass vial (type 1) and sealed with sterile closures and overseals.

Example 19: Intramuscular Injection

| Compound of the invention | 200 mg |
| Benzyl Alcohol | 0.10 g |
| Glycofurol 75 | 1.45 g |
| Water for injection q.s to | 3.00 mL |

The compound of the invention is dissolved in the glycofurol. The benzyl alcohol is then added and dissolved, and water added to 3 ml. The mixture is then filtered through a sterile micropore filter and sealed in sterile 3 ml glass vials (type 1).

Example 20

Syrup Formulation

| Compound of invention | 250 mg |
| Sorbitol Solution | 1.50 g |
| Glycerol | 2.00 g |
| Sodium benzoate | 0.005 g |
| Flavour | 0.0125 mL |
| Purified Water q.s. to | 5.00 mL |

The compound of the invention is dissolved in a mixture of the glycerol and most of the purified water. An aqueous solution of the sodium benzoate is then added to the solution, followed by addition of the sorbitol solution and finally the flavour. The volume is made up with purified water and mixed well.

The invention claimed is:
1. A compound which is an isoxazolyl imidazopyridine of formula (I):

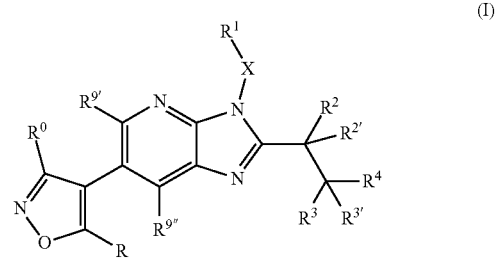

wherein:
R$^0$ and R, which are the same or different, are each H or C$_{1-6}$ alkyl;
R$^{9'}$ and R$^{9''}$, which are the same or different, are each H or F;
R$^2$ and R$^{2'}$, which are the same or different, are each H or C$_{1-6}$ alkyl; or R$^2$ and R$^{2'}$ form, together with the C atom to which they are attached, a C$_{3-6}$ cycloalkyl group;
R$^3$ and R$^{3'}$, which are the same or different, are each H, C$_{1-6}$ alkyl, OH or F;
R$^4$ is phenyl or a 5- to 12-membered N-containing heteroaryl group and is unsubstituted or substituted;
alk is C$_{1-6}$ alkylene;
R' is C$_{1-6}$ alkyl;
n is 0 or 1; and
X—R$^1$ is selected from the following structures:

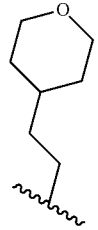 [SMILES: *CCC1CCOCC1]

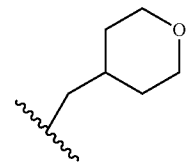 [SMILES: *CC1CCOCC1]

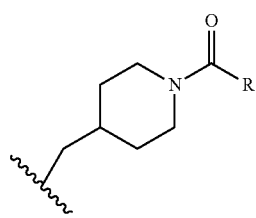
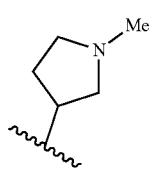 [SMILES: *C1CCN(C)C1]
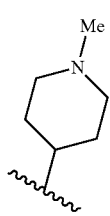
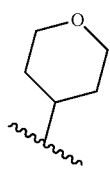
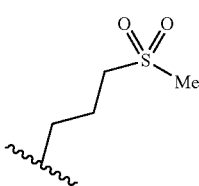 [SMILES: *CCCS(C)(=O)=O]
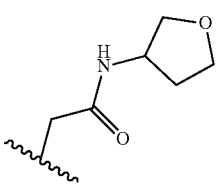 [SMILES: *CC(=O)NC1CCOC1]
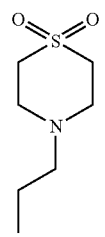
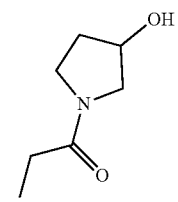
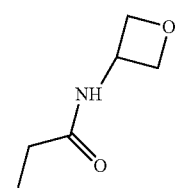
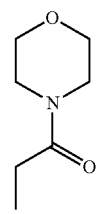
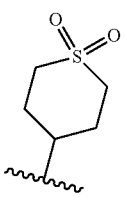 [SMILES: *C1CCS(=O)(=O)CC1]
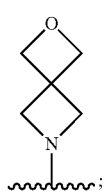 [SMILES: *N1CC2(COC2)C1]
or a pharmaceutically acceptable salt thereof.
2. A compound according to claim 1, wherein the isoxazolyl imidazopyridine has the following formula (Ia):

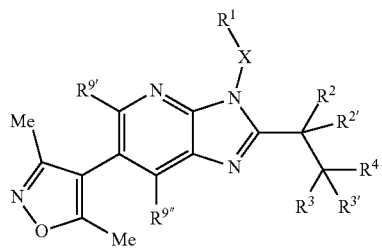

wherein each of R⁹', X—R¹, R², R²', R³, R³' and R⁴ is as defined in claim 1 for formula (I).

3. A compound according to claim 1 wherein the isoxazolyl imidazopyridine has the following formula (Ib):

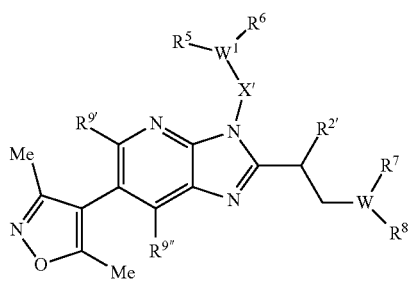

wherein:
R⁹' and R⁹'' are as defined above for formula (I);
W is N or C;
R²' is H, Me or Et;
R⁷ and R⁸ form, together with the C or N atom to which they are attached, a group selected from phenyl, pyridinyl, pyrimidinyl, quinolinyl, isoquinolinyl, pyrrolopyridinyl and quinoxalinyl, which group is unsubstituted or substituted; and

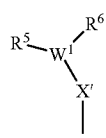

is selected from the following structures:

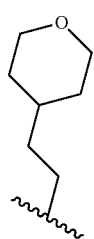 [SMILES: *CCC1CCOCC1]

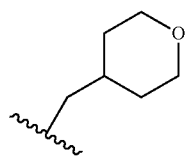 [SMILES: *CC1CCOCC1]

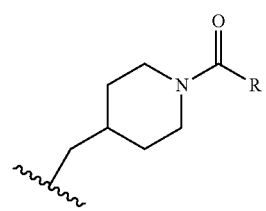

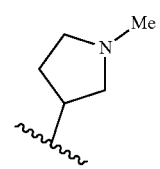 [SMILES: *C1CCN(C)C1]

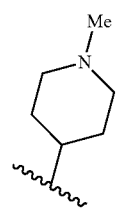 [SMILES: *C1CCN(C)CC1]

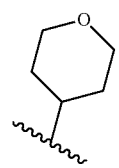 [SMILES: *C1CCOCC1]

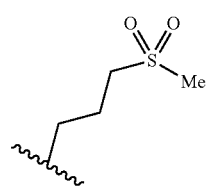 [SMILES: *CCCS(C)(=O)=O]

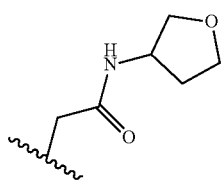 [SMILES: *CC(=O)NC1CCOC1]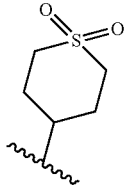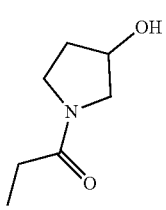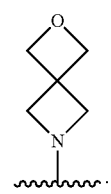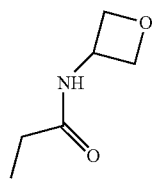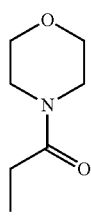

4. A pharmaceutical composition which comprises a pharmaceutically acceptable carrier or diluent and, as an active ingredient, a compound as defined in claim 1.

5. A compound according to claim 1, which is selected from:

4-(2-(4-methoxyphenethyl)-3-(2-(tetrahydro-2H-pyran-4-yl)ethyl)-3H-imidazo[4,5-b]pyridin-6-yl)-3,5-dimethylisoxazole;

4-(2-(3-fluoro-4-methoxyphenethyl)-3-(2-(tetrahydro-2H-pyran-4-yl)ethyl)-3H-imidazo[4,5-b]pyridin-6-yl)-3,5-dimethylisoxazole;

4-(2-(6-(3,5-dimethylisoxazol-4-yl)-2-(3-fluoro-4-methoxyphenethyl)-3H-imidazo[4,5-b]pyridin-3-yl)ethyl)thiomorpholine 1,1-dioxide;

2-(6-(3,5-dimethylisoxazol-4-yl)-2-(3-fluoro-4-methoxyphenethyl)-3H-imidazo[4,5-b]pyridin-3-yl)-N-(tetrahydrofuran-3-yl)acetamide;

2-(6-(3,5-dimethylisoxazol-4-yl)-2-(3-fluoro-4-methoxyphenethyl)-3H-imidazo[4,5-b]pyridin-3-yl)-1-(4-hydroxypiperidin-1-yl)ethan-1-one;

2-(6-(3,5-dimethylisoxazol-4-yl)-2-(3-fluoro-4-methoxyphenethyl)-3H-imidazo[4,5-b]pyfidin-3-yl)-N-(oxetan-3-yl)acetamide;

4-(2-(6-(3,5dimethylisoxazol-4-yl)-2-(4-methoxyphenethyl)-3H-imidazo[4,5-b]pyridin-3-yl)ethyl)thiomorpholine 1,1-dioxide;

2-(6-(3,5-dimethylisoxazol-4-yl)-2-(3-fluoro-4-methoxyphenethyl)-3H-imidazo[4,5-b]pyridin-3-yl)-1-morpholinoethan-1-one;

2-(6-(3,5-dimethylisoxazol-4-yl)-2-(3-fluoro-4-methoxyphenethyl)-3H-imidazo[4,5-b]pyridin-3-yl)-N-(tetrahydro-2H-pyran-4-yl)acetamide;

2-(6-(3,5-dimethylisoxazol-4-yl)-2-(3-fluoro-4-methoxyphenethyl)-3H-imidazo[4,5-b]pyridin-3-yl)-1-(3-hydroxypyrrolidin-1-yl)ethan-1-one;

and the pharmaceutically acceptable salts thereof.

\* \* \* \* \*

UNITED STATES PATENT AND TRADEMARK OFFICE
CERTIFICATE OF CORRECTION

PATENT NO. : 10,428,065 B2
APPLICATION NO. : 15/567750
DATED : October 1, 2019
INVENTOR(S) : Neil Anthony Pegg et al.

Page 1 of 1

It is certified that error appears in the above-identified patent and that said Letters Patent is hereby corrected as shown below:

In the Claims

In Claim 2, at Column 57, Line 13, "$R^{9''}$," should be added after --$R^{9'}$,--; and In Claim 5, at Column 60, Line 41, "pyfidin-3-yl" should read --pyridin-3-yl--.

Signed and Sealed this
Third Day of December, 2019

Andrei Iancu
*Director of the United States Patent and Trademark Office*